(12) United States Patent
Yamakawa et al.

(10) Patent No.: US 9,592,021 B2
(45) Date of Patent: Mar. 14, 2017

(54) X-RAY CT DEVICE, AND METHOD

(75) Inventors: Keisuke Yamakawa, Tokyo (JP); Hironori Ueki, Yokohama (JP); Yukiko Ueki, legal representative, Yokohama (JP)

(73) Assignee: HITACHI, LTD., Tokyo (JP)

( * ) Notice: Subject to any disclaimer, the term of this patent is extended or adjusted under 35 U.S.C. 154(b) by 370 days.

(21) Appl. No.: 14/000,617

(22) PCT Filed: Dec. 22, 2011

(86) PCT No.: PCT/JP2011/079870
§ 371 (c)(1),
(2), (4) Date: Aug. 21, 2013

(87) PCT Pub. No.: WO2012/127761
PCT Pub. Date: Sep. 27, 2012

(65) Prior Publication Data
US 2014/0198892 A1    Jul. 17, 2014

(30) Foreign Application Priority Data

Mar. 22, 2011  (JP) ................... 2011-063326

(51) Int. Cl.
*A61B 6/03*  (2006.01)
*G06T 11/00*  (2006.01)
*A61B 6/00*  (2006.01)

(52) U.S. Cl.
CPC ........... *A61B 6/5252* (2013.01); *A61B 6/03* (2013.01); *A61B 6/032* (2013.01); *A61B 6/5258* (2013.01); *G06T 11/006* (2013.01); *A61B 6/5205* (2013.01)

(58) Field of Classification Search
CPC ........... A61B 6/027; A61B 6/037; A61B 6/06; A61B 6/08; A61B 6/32; A61B 6/40;
(Continued)

(56) References Cited

U.S. PATENT DOCUMENTS 6,600,802 B1 *  7/2003  Hsieh .................................. 378/4
6,801,646 B1 * 10/2004  Pena et al. ...................... 382/131
(Continued)

FOREIGN PATENT DOCUMENTS

JP    4-295340    10/1992
JP    5-192325    8/1993
(Continued)

OTHER PUBLICATIONS

Andy Ziegler et al., Iterative reconstruction of a region of interest for transmission tomography, Medical Physics, Apr. 2008, pp. 1317-1327, vol. 35, No. 4.

*Primary Examiner* — Glen Kao
(74) *Attorney, Agent, or Firm* — Baker Botts L.L.P.

(57) ABSTRACT

The background projection data of a background region CT image in the X-ray emission path is calculated. Using measurement projection data and background projection data, the measurement projection data of local regions is calculated. Local region CT images are calculated on the basis of local measurement projection data, and the projection data of a local region CT image in the X-ray emission path is calculated. On the basis of local calculation projection data and local measurement projection data, local CT images are iteratively corrected. When creating background region CT images or calculating background projection data, the cause of calculation accuracy deterioration is eliminated by the use of processing such as smoothing, and without deterioration of CT value accuracy in regions other than the target region, a high-quality CT image is obtained.

15 Claims, 14 Drawing Sheets

(58) Field of Classification Search
CPC ... G06T 11/006; G06T 2211/424; G21K 1/02; H01J 35/16; H01J 2235/081; H01J 2235/086; H01J 2235/087; H01J 2235/168

See application file for complete search history.

(56) References Cited

U.S. PATENT DOCUMENTS

| | | | |
|---|---|---|---|
| 2003/0007601 A1* | 1/2003 | Jaffray | A61B 6/032 378/65 |
| 2003/0095692 A1* | 5/2003 | Mundy et al. | 382/128 |
| 2009/0225934 A1* | 9/2009 | Hugg et al. | 378/20 |
| 2009/0278953 A1* | 11/2009 | Velthoven et al. | 348/222.1 |
| 2010/0322514 A1 | 12/2010 | Koehler | |

FOREIGN PATENT DOCUMENTS

| | | |
|---|---|---|
| JP | 2003-144430 | 5/2003 |
| JP | 2006-25868 | 2/2006 |
| JP | 2007-97977 | 4/2007 |
| JP | 2010-514530 | 5/2010 |

\* cited by examiner

THRESHOLD
DECISION (a): LARGE FOV IMAGE (b): BACKGROUND IMAGE BY EMBODIMENT 4

(c): SMALL FOV IMAGE BY EMBODIMENT 4

(d): CONVENTIONAL METHOD (e): EMBODIMENT 4

(a): ENLARGED DIAGRAM OF LARGE FOV IMAGE BY CONVENTIONAL METHOD (b): ENLARGED DIAGRAM OF LARGE FOV IMAGE BY EMBODIMENT 7

X-RAY CT DEVICE, AND METHOD

CROSS-REFERENCE TO RELATED APPLICATIONS

This application claims priority to International Patent Application No. PCT/JP2011/079870, filed Dec. 22, 2011, which claims the benefit of JP Application No. 2011-063326, filed Mar. 22, 2011, which are both hereby incorporated by reference in their entirety.

TECHNICAL FIELD

The present invention relates to an X-ray CT device, and pertains to an image generation technology for iteratively correcting a CT image such that measurement projection data which has been measured becomes equal to calculation projection data that the CT image has been forward projected.

BACKGROUND ART

An X-ray CT (Computed Tomography) device is a device for calculating an X-ray absorption rate of each point from X-ray projection data obtained by imaging a subject from many directions to obtain an distribution image of X-ray absorption rate (hereinafter, referred to as a CT image) consisting of a plurality of pixels as a tomographic image of the subject. The CT image obtained by the present device can accurately and rapidly diagnose a patient's illness and is useful clinically in medical settings. However, radiation exposure of a fixed amount ensues in order to obtain a high quality image required for a diagnosis of a doctor. On the other hand, a ratio of noise to a signal is increased and a linear artifact and granular noise which would be a cause for an erroneous diagnosis are frequently generated as an exposure dose is reduced in order to realize low-dose exposure. Accordingly, if the artifact and the noise could be reduced in low-dose imaging, a high-quality diagnosis and low-dose exposure can be realized. In order to solve this problem, in a technology of Patent Document 1, an iterative reconstruction method of iteratively correcting a CT image such that measurement projection data becomes equal to calculation projection data is proposed.

On the other hand, in the X-ray CT device, extensive reconstruction is utilized in order to image a local region of a subject required for a diagnosis at a high resolution. However, since the general iterative reconstruction method needs to image the entire subject including a bed, a fixture and the like, extensive reconstruction cannot be applied.

In order to solve this subject, in the document of Non patent, first, a CT image (hereinafter, referred to as a large FOV (Field of View) image) is reconstructed on condition that the entire subject is included. Next, a background image of a background region other than a local region of the subject required for the diagnosis is forward projected, and the obtained background projection data is subtracted from the measurement projection data. Measurement projection data (hereinafter, referred to as local measurement projection data) which is required to iteratively correct a CT image (hereinafter, referred to as a small FOV image) of the local region can be obtained by this processing.

PRIOR ART DOCUMENT

Patent Document

Patent Document 1: Japanese Patent Application Laid-Open No. 2006-25868

Non Patent Document

Non Patent Document 1: Andy Ziegler, et al., "Iterative reconstruction of a region of interest for transmission tomography", Med. Phys. 35(4), p 1317-1317, 2008

SUMMARY OF THE INVENTION

Problem to be Solved by the Invention

The image quality of the small FOV image by the above-mentioned extensive reconstruction depends on the accuracy of the local measurement projection data. As a cause to determine the accuracy of this local measurement projection data, there is the accuracy of the large FOV image or the background projection data. For example, a case where a false image such as a streak artifact or the like is generated in the large FOV image will be given. An error of the large FOV image caused by this false image causes deterioration of the accuracy of the local measurement projection data through the forward projected and calculated background projection data. As a result, since the small FOV image is corrected using the local measurement projection data of low accuracy, there is a subject that the CT value accuracy of the false image or the like is deteriorated.

An object of the present invention is to provide X-ray CT device and method capable of solving the above-mentioned problem.

Means for Solving the Problems

In order to attain the above-mentioned object, the present invention provides an X-ray CT device which includes an X-ray generation unit for generating an X-ray, an X-ray detection unit for detecting the X-ray after transmitted through a subject, a projection data measurement unit for generating measurement projection data from a detection signal of the X-ray detection unit which has been measured by rotating the X-ray generation unit and the X-ray detection unit, and an image generation unit for generating a CT image from the measurement projection data, wherein the image generation unit includes, a background image creation unit for creating a CT image of a background region from the measurement projection data, a background projection data calculation unit for calculating background projection data of the CT image of the background region on a path connecting the X-ray generation unit and the X-ray detection unit, a local measurement projection data calculation unit for calculating local measurement projection data of a local region using the measurement projection data and the background projection data, a local image calculation unit for calculating the CT image of the local region from the local measurement projection data, a local projection data calculation unit for calculating local calculation projection data of the CT image of the local region on the path connecting the X-ray generation unit and the X-ray detection unit, a local image correction unit for iteratively correcting the CT image of the local region on the basis of the local calculation projection data obtained by the local projection image calculation unit and the local measurement projection image, and a cause elimination unit for eliminating a cause to deteriorate calculation accuracy of the CT image of the background region or the background projection data.

In addition, in order to attain the above-mentioned object, the present invention provides an image generation method for an image generation device equipped with a processing unit, for generating a CT image from measurement projection data of an X-ray CT device, wherein the processing unit creates a CT image of a background region from the measurement projection data, calculates background projection data of the CT image of the background region on an X-ray irradiation path, and calculates local measurement projection data of a local region using the measurement projection data and the background projection data, calculates a CT image of the local region from the obtained local measurement projection data, calculates local calculation projection data of the CT image of the local region on the X-ray irradiation path, iteratively corrects the CT image of the local region on the basis of the local calculation projection data which has been obtained and the local measurement projection data, and eliminates a cause to deteriorate calculation accuracy when creating the CT image of the background region, or calculating the background projection data.

Advantage of the Invention

According to the present invention, the CT value accuracy deterioration of the small FOV image can be prevented by eliminating the cause to deteriorate the accuracy of the large FOV image or the background projection data. In addition, there is such an advantage that the CT value accuracy is not erroneously deteriorated by not processing the one other than the region which would be the cause.

BEST MODE FOR CARRYING OUT THE INVENTION

Figure 1:
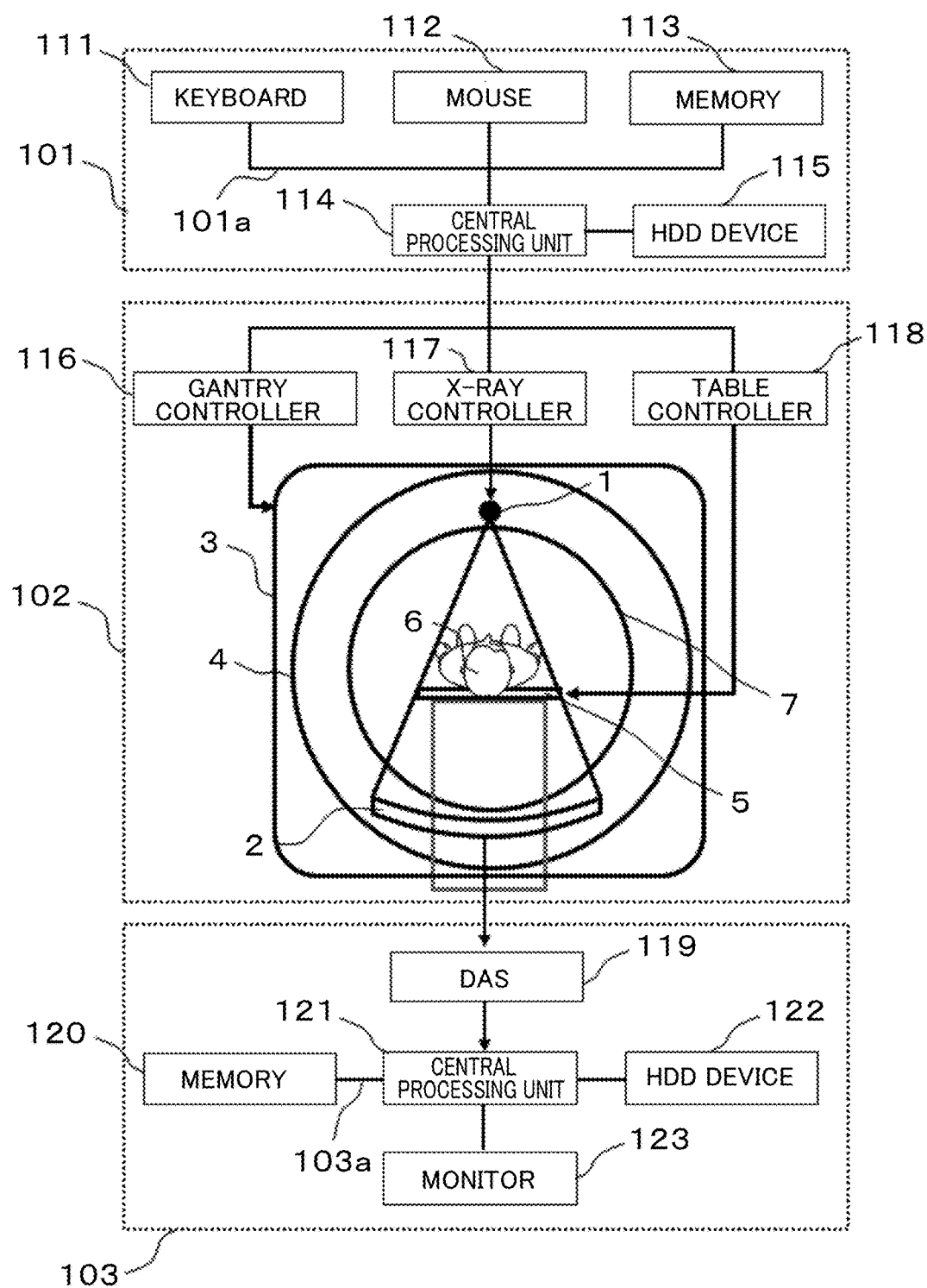
FIG. 1 is a diagram for explaining a hardware configuration of respective units of a CT device in an embodiment 1.

In the following, various embodiments of the present invention will be described in accordance with the drawings. Each functional element configuring the various embodiments disclosed in the present specification will be sometimes called a "function, a "means", a "unit" and the like. For example, they are an "image calculation function", an "image calculation means", an "image calculation unit" and the like.

In the following, prior to description of the embodiments of the present invention, causes to determine the accuracy of the local measurement projection data, that is, calculation accuracy of a large FOV image or background projection data will be described.

As a first cause to determine the accuracy, the large FOV image is sometimes reconstructed by using a conventional Ramp filter or Sheep-Logan filter. At that time, measurement projection data is suddenly blocked with the Nyquist frequency of the reconstruction filter. Therefore, a false image is generated around a boundary part of a subject and air or the like where a CT value difference is large. As a second cause, the large FOV image cannot acquire projection data sufficient for high quality reconstruction in a case where the number of acquired projections in one rotation is little. Structural strain, a false image and the like are generated under the influence of this. As a third cause, the large FOV image sometimes exhibits a sudden change in X-ray energy spectrum around a high absorbent such as metal or the like. Due to this cause, a metal artifact is generated. As a fourth cause, a case where the large FOV image is an image which is large in size [mm/pixel] of one pixel and low in resolution can be given. Under this condition, a difference with a real subject is large and the CT value accuracy will be deteriorated under the influence of a quantization error.

Embodiment 1

An X-ray CT device of a first embodiment will be described in detail with reference to the drawings. The X-ray CT device of the first embodiment is configured by an X-ray generation unit for generating an X-ray, an X-ray detection unit for detecting the X-ray after transmitted through a subject, a projection data measurement unit for generating measurement projection data from a detection signal of the above-mentioned X-ray detection unit which has been measured by rotating the above-mentioned X-ray generation unit and the above-mentioned X-ray detection unit, and an image generation unit for performing image generation from the measurement projection data.

The image generation unit of the present embodiment is configured by a background image creation unit for creating a CT image of a background region from the measurement projection data, a background projection data calculation unit for calculating projection data as an integrated value of a background image on a path connecting the X-ray generation unit and the X-ray detection unit, a local measurement projection data calculation unit for subtracting the background projection data from the measurement projection data to calculate measurement projection data of a local region, a local image calculation unit for calculating a CT image of the local region which is an X-ray absorption rate distribution from the local measurement projection data, a local projection data calculation unit for calculating projection data as an integrated value of a local CT image on the path connecting the X-ray generation unit and the X-ray detection unit, and a local image correction unit for iteratively correcting the local CT image such that the local calculation projection data becomes equal to the local measurement projection data.

Then, the background image creation unit has an image calculation unit for calculating the CT image which is the X-ray absorption rate distribution from the measurement projection data, a projection data calculation unit for calculating the projection data as the integrated value of the CT image on the path connecting the X-ray generation unit and the X-ray detection unit, and an image correction unit for iteratively correcting the CT image such that the calculation projection data becomes equal to the measurement projection data, and divides the corrected CT image into the local region and the background region other than that and replaces a pixel value of the local region with an X-ray absorption rate of a fixed value to create an image. The above-mentioned image calculation unit is equipped with a cause elimination unit for eliminating a cause to deteriorate the calculation accuracy of the CT image.

FIG. 1 is a diagram showing a hardware configuration which implements an X-ray CT device loaded with iterative reconstruction software of the embodiment 1. The device in FIG. 1 is configured by an input means 101 for inputting imaging conditions such as X-ray irradiation conditions and image reconstruction conditions, an imaging means 102 for performing control of imaging, X-ray irradiation and detection, and an image generation means 103 for performing correction and image reconstruction on a detected signal to output an image. The image generation means 103 corresponds to the above-mentioned image generation unit. Incidentally, the input means 101 and the image generation means 103 need not be configured integrally with a main device having an imaging function and may perform processing, for example, over a network. In addition, hardware such as an input/output unit which configures the input means 101 and the image generation means 103, a processing unit and a storage unit may be used in common.

In the input means 101, input of the imaging conditions can be implemented by a keyboard 111, a mouse 112, a pen tablet, a touch panel and the like, and further by a monitor whose illustration is omitted and the like. Data input by the input means 101 sends a signal to the imaging means 101 by developing and activating a predetermined program in a central processing unit (CPU: Central Processing Unit) 114 which is the processing unit, and a memory 113, an HDD (Hard Disk Drive) device 115 and the like configuring the storage unit. The above-mentioned respective constitutional elements are connected together via a data bus 101a.

In the imaging means 102 in FIG. 1, control of imaging can be implemented respectively by an X-ray controller 117, a gantry controller 116, and a table controller 118 when operating an X-ray tube 1, a gantry 3, and a table 5. Next, irradiation and detection of the X-ray can be implemented by the X-ray tube 1 and an X-ray detector 2. A typical example of a distance between an X-ray generation point of the X-ray tube 1 and an X-ray input plane of the X-ray detector 2 is 1000 [mm]. A circular opening 7 for disposing a subject 6 and the table 5 is installed in the center of the gantry 3. A typical example of the diameter of the opening 7 is 700 [mm]. A typical example of the time required for rotation of a rotating plate 4 is 1.0 [s] A well-known X-ray detector configured by a scintillator, a photodiode or the like is used as the X-ray detector 2. The X-ray detector 2 has many not shown detection elements which are equally distant from the X-ray tube 1 in an arc-shape, and a typical example of the number of elements (hereinafter, referred to as the number of channels) is 950. A typical example of the size of each detection element in a channel direction is 1 [mm]. The number of acquired projections in one rotation of the imaging means 102 is 900 and imaging is performed once every time the rotating plate 4 rotates by 0.4 degrees. Incidentally, the above mentioned respective specifications are not limited to these values and can be changed variably in accordance with a configuration of the X-ray CT device.

In the image generation means 103 which is the image generation unit, a signal detected by the X-ray detector 2 of the imaging means 102 is converted into a digital signal by a data acquisition system (DAS: Data Acquisition System) 119. Next, correction and image reconstruction can be implemented on the converted digital signal by developing and activating a predetermined program in a central processing unit (CPU) 121 which is the processing unit, and a memory 120 configuring the storage unit, and data saving and input/output can be implemented by an HDD device 122 and the like. Display of the CT image subjected to image reconstruction can be implemented by a monitor 123 such as a liquid crystal display, a CRT or the like which is the display unit. Incidentally, the above-mentioned respective constitutional elements are connected together via a data bus 103a. As described above, the CPU, the memory, the monitor and the like can be commonly used by the input means 101 and the image generation means 103.

Figure 2:
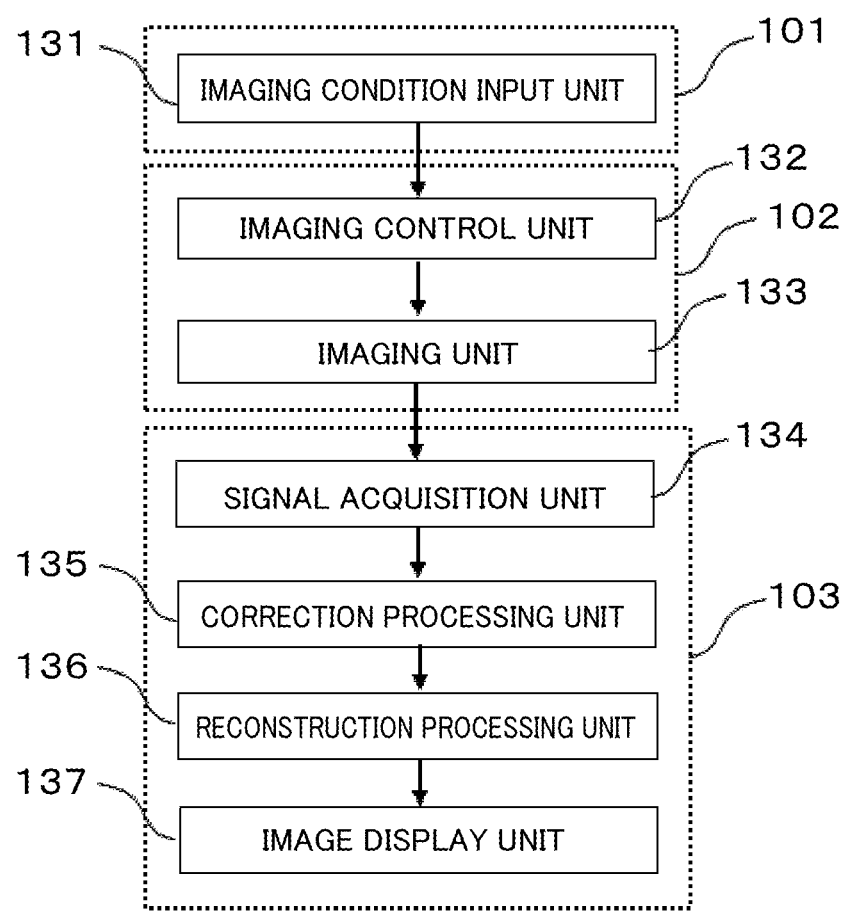
FIG. 2 is a functional block diagram for explaining a flow of imaging in the embodiment 1.

FIG. 2 is a functional block diagram for explaining a flow of imaging of the X-ray CT device loaded with the iterative reconstruction software of the embodiment 1. In the functional block in FIG. 2, the input means 101 is configured by an imaging condition input unit 131 for inputting the imaging conditions. The imaging means 102 is configured by an imaging control unit 132 for controlling imaging on the basis of the imaging conditions input by the above-mentioned imaging condition input unit 131, and an imaging unit 133 for performing irradiation and detection of the X-ray. The image generation means 103 is configured by a signal acquisition unit 134 for converting the detected signal into the digital signal, a correction processing unit 135 for performing correction on the above-mentioned digital signal, a reconstruction processing unit 136 for performing image reconstruction on the corrected projection data, and an image display unit 137 for outputting the reconstructed CT image.

Figure 3:
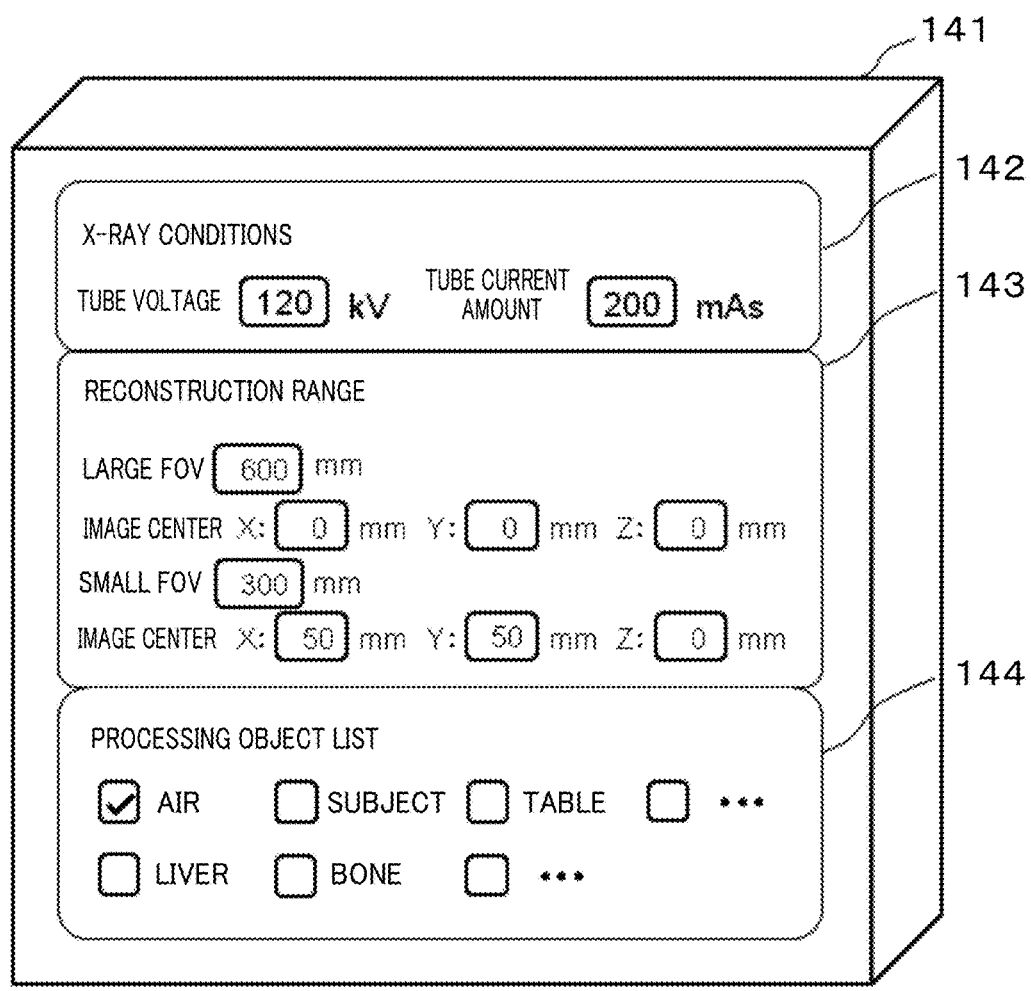
FIG. 3 is a diagram for explaining a screen example of an imaging condition input unit in the embodiment 1.

Next, the flow of imaging of the X-ray CT device will be described using FIG. 2. FIG. 3 is a diagram showing one example of a monitor screen of the monitor of the imaging condition input unit 131 shown in FIG. 2. An operator sets an X-ray condition, a reconstruction range and a processing object list using a monitor screen 141, and using the mouse 112, the keyboard 111 or the like. The present screen is configured by an X-ray condition 142 for setting the tube voltage and the tube current amount corresponding to the energy and output amount of the X-ray to be irradiated, a reconstruction range 143 for setting the visual field of the reconstructed image and the central position of the reconstructed image, and a processing object list 144 for selecting an object to be subjected to smoothing which is a cause elimination function.

In the X-ray condition 142 in the present embodiment, a typical example of the tube voltage value that the operator sets is 120 [kV] with the tube current amount 200 [mAs]. Although in the present embodiment, the X-ray having one kind of energy spectrum has been supposed, in a multi-energy CT using two or more kinds of X-rays, it can be similarly performed by adding the items of the tube voltage and the tube current amount.

For the reconstruction range 143 in FIG. 3, the operator sets the visual field [mm] of a large FOV image (hereinafter, referred to as a large FOV) and the central position of the reconstructed image, the visual field [mm] of a small FOV image (hereinafter, referred to as a small FOV) and the central position of the reconstructed image. The FOV in the present embodiment is defined by a square and is set as the large FOV 600 [mm] and the small FOV 300 [mm]. At the central position of the reconstructed image, the large FOV is set equally to the rotation center as X=Z=0 [mm] and the small FOV is set at a position apart from the rotation center as X=50 [mm], Y=50 [mm] and Z=0 [mm]. However, the large FOV and the small FOV are not limited to the square and the present embodiment can be similarly applied to arbitrary shapes such as a circle, a rectangle, a cube, a rectangular parallelepiped, a sphere and the like.

The processing object list 144 indicates an object to which smoothing for implementing the cause elimination function is to be applied in the large FOV image in the present embodiment. In the present embodiment, air is selected as shown in FIG. 3. At that time, a part may be selected not limited to the subject. For example, the part such as the chest, the abdomen, the head, the neck, the spine, the hip joints, the limbs or the like may be selected. In addition, there may be a tissue such as the liver, a bone, the coronary artery or the like not limited to the part. In a case where an object in the object list 144 is not selected, smoothing is not applied.

FIG. 3 is one example of the X-ray condition, the reconstruction range, and the processing object list and they need not be limited to the configuration of the present screen. In addition, in a case where setting of the X-ray condition, the reconstruction range and the processing object list is saved in advance in the HDD device 115, the operator need not input it every time.

Next, in FIG. 2, the imaging means 103 performs X-ray imaging in accordance with the imaging condition input by the imaging condition input unit 131. First, the operator instructs start of imaging after an imaged position of the subject 6 has been designated by using the mouse 112, the keyboard 111 or the like. When the start of imaging is instructed, the table 5 moves the subject 6 in a direction almost vertical to the rotating plate 4 by the table controller 118 of the imaging control unit 132. Then, it stops movement at a time that the imaged position of the subject 6 has matched the above-mentioned set values and terminates arrangement of the subject 6.

On the other hand, the gantry controller 116 of the imaging control unit 132 starts rotation of the rotating plate 4 via a driving motor simultaneously with instruction of the start of imaging. At a time that the rotation of the rotating plate 4 enters a constant-speed state and the above-mentioned arrangement of the subject 6 has been terminated, the gantry controller 116 instructs an X-ray irradiation timing of the X-ray tube 1 of the imaging unit and an imaging timing of the X-ray detector 2 of the imaging unit to start imaging.

In the present embodiment, for example, it determines the energy spectrum and the output amount of the X-ray to be irradiated according to the tube voltage and the tube current amount of the X-ray tube that the operator has set.

Incidentally, although in the present embodiment, the X-ray having one kind of the energy spectrum has been used, it can be also applied to a multi-energy CT that an X-ray having two or more kinds of the energy spectra is irradiated by switching the tube voltage at a high speed at each rotation to obtain imaging data.

Next, in FIG. 2, in the X-ray detector 2 of the imaging unit 133, an X-ray photon transmitted through the subject 6 is detected and is converted into the digital signal by the DAS 119 of the signal acquisition unit 134. X-ray detection data which has been obtained is saved in the memory 120. In the correction processing unit 135, correction such as offset correction for calibrating the X-ray signal to zero, well-known air calibration processing for correcting the sensitivity between detectors or the like is performed on this data to obtain the measurement projection data of the subject 6. This measurement projection data obtained by the signal acquisition unit 134 and the correction processing unit 135 is sent to the reconstruction processing unit 136 following the correction processing unit 135.

Figure 4:
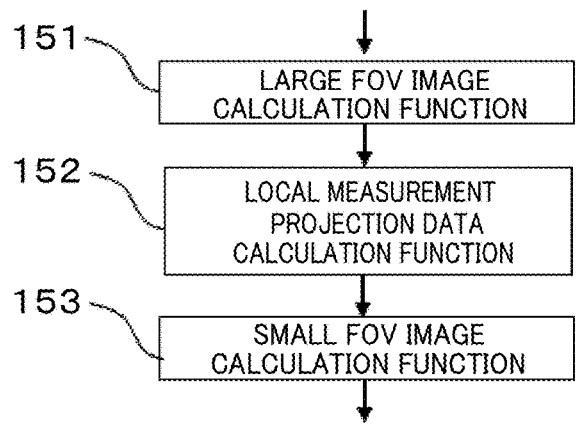
FIG. 4 is a diagram for explaining respective functions of a reconstruction processing unit in the embodiment 1.

Next, as shown in FIG. 4, the reconstruction processing unit 136 is configured by a large FOV image calculation function 151 for calculating the large FOV image, a local measurement projection data calculation function 152 for calculating the local measurement projection data, and a small FOV image calculation function 153 for calculating the small FOV image. The correction processing unit 135 and the reconstruction processing unit 136 are implemented by program processing of the above-mentioned CPU 121. In the following, one example of the processing operation of the reconstruction processing unit 136 will be described in detail using FIG. 5 to FIG. 7.

Figure 5:
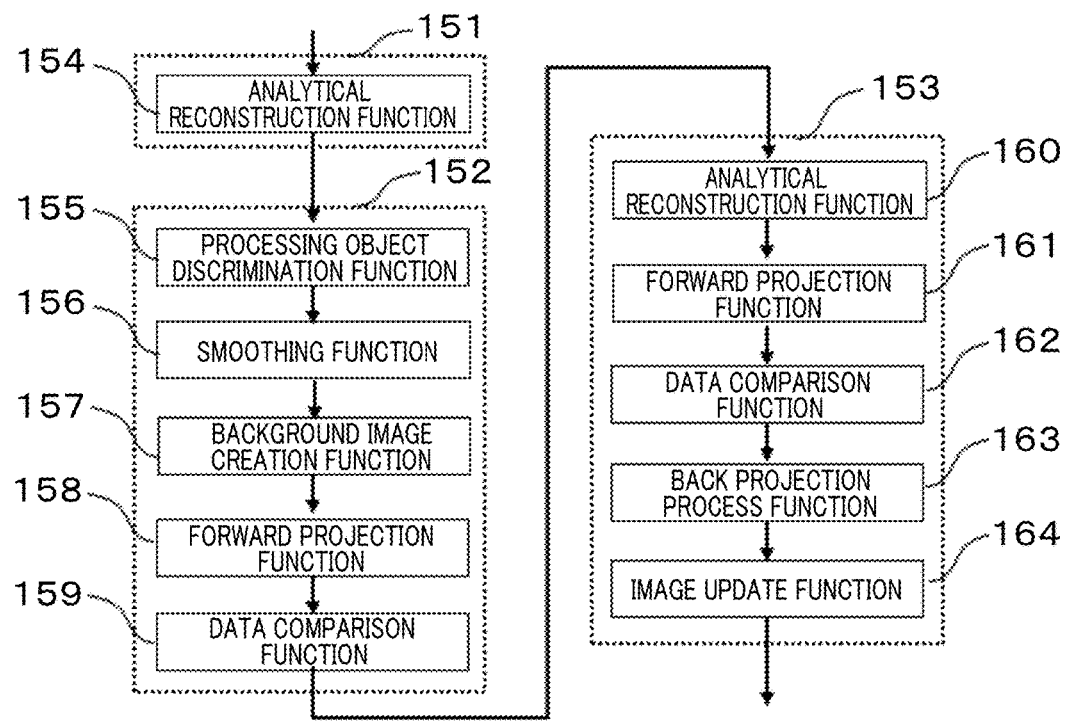
FIG. 5 is a diagram for explaining respective functions of a reconstruction processing unit in the embodiment 1.

As shown in FIG. 5, each function block of the reconstruction processing unit 136 in FIG. 4 is configured by being divided into a plurality of small function blocks as shown in FIG. 5 and can be implemented by a plurality of program units corresponding to the small function blocks. With respect to each function block, description will be made by using a processing flow in FIG. 6. First, the large FOV image calculation function 151 in FIG. 4 will be described.

Figure 6:
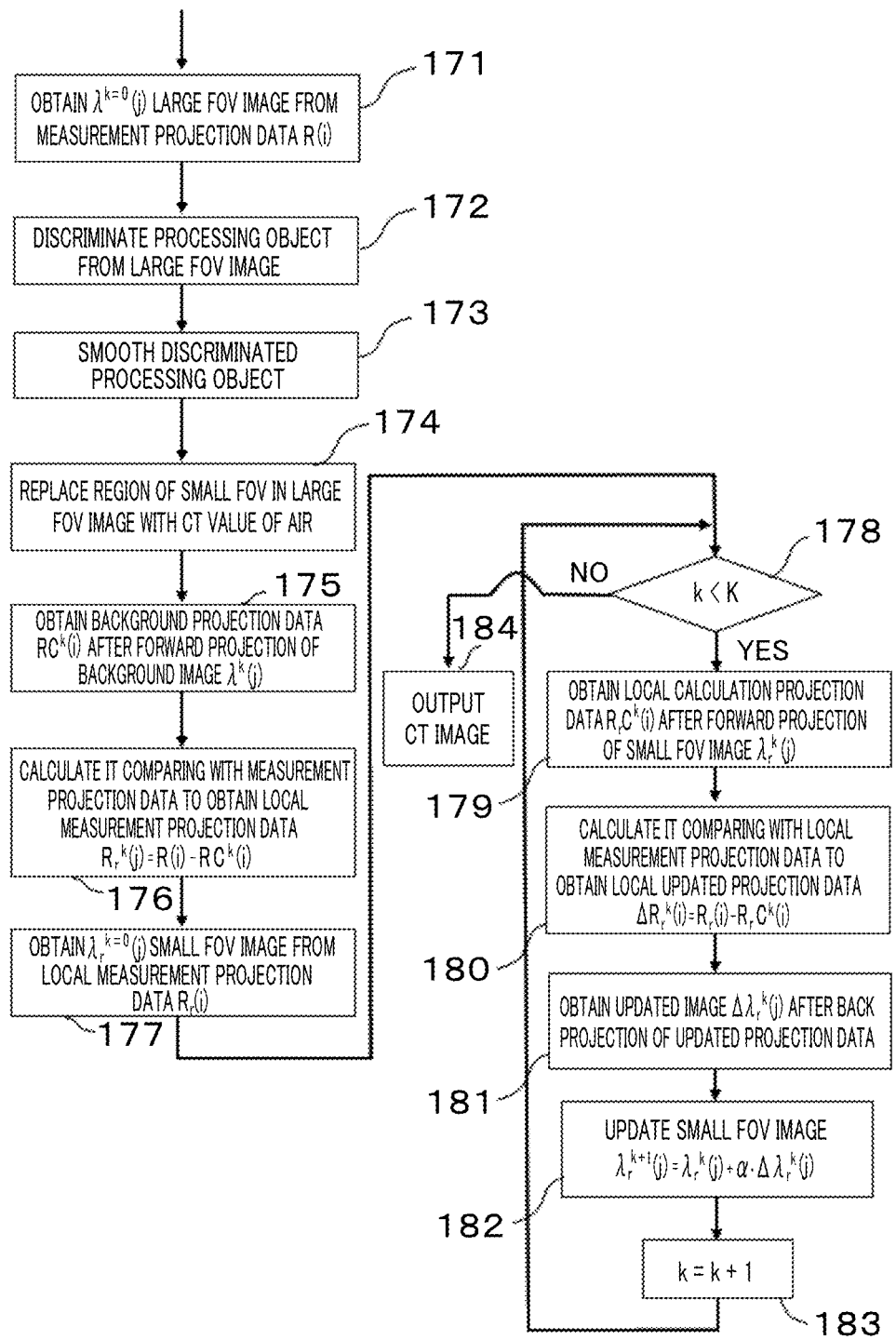
FIG. 6 is a diagram for explaining calculation procedure of an iterative reconstruction method in the embodiment 1.

As shown in FIG. 6, an analytical reconstruction function 154 corresponding to the large FOV image calculation function 151 calculates a large FOV image $\lambda^{k=0}(j)$ indicating the CT value of the subject using a well-known analytical reconstruction method such as Feldkamp method or the like for measurement projection data R(i) corrected by the correction processing unit 135 in step 171. i and j respectively denote a detector number and a pixel number. At that time, the large FOV image $\lambda^{k=0}(j)$ may be repetitively corrected using a well-known iterative reconstruction method by the loaded iterative reconstruction software.

It is assumed that $\lambda^k(j)$ in step 171 that the analytical reconstruction function 154 executes indicates a pixel value of a pixel j of the large FOV image in an updating number k in calculation and is configured by J pixels. The small FOV image is applicable not only to a general two-dimensional (x, y directions) tomographic image but also to one-dimensional data (the x direction), three-dimensional data (the x, y, z directions) that images are superimposed in an antero-posterior direction z, or even four-dimensional data (the x, y, z, t directions) that a time direction t is taken into account in the three-dimension.

The large FOV image calculation function 151 which is implemented by this analytical reconstruction function 154 corresponds to the image calculation unit for calculating the CT image which is the X-ray absorption rate distribution from the above-mentioned measurement projection data. In addition, the iterative reconstruction method by the iterative reconstruction software is implemented by the projection data calculation unit for calculating the projection data as the integrated value of the CT image on the path connecting the above-mentioned X-ray generation unit and the X-ray detection unit, and the image correction unit for iteratively correcting the CT image such that the calculation projection data becomes equal to the measurement projection data.

Next, the local measurement projection data calculation function 152 in FIG. 4 will be described. As shown in FIG. 5, the local measurement projection data calculation function 152 is implemented by a processing object discrimination function 155, a smoothing function 156 which is a cause elimination function, a background image creation function 157, a forward projection function 158, and a data comparison function 159. Incidentally, the background image means an image of the background region except for the local region showing the small FOV image in the large FOV image.

Figure 7:
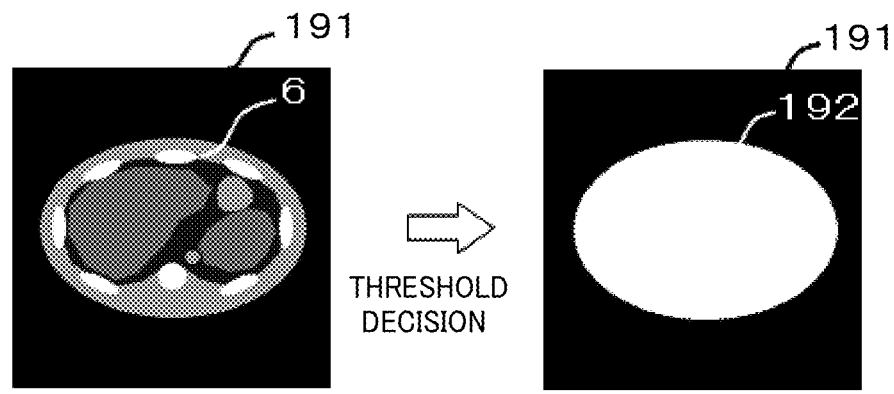
FIG. 7 is a diagram for explaining discrimination of a processing object by threshold decision in the embodiment 1.

First, the processing object discrimination function 155 discriminates the object selected by the processing object list 144 from the large FOV image in step 172 in FIG. 6. Since in the present embodiment, air is selected as mentioned above, it discriminates air and a region other than air. As a discrimination method, a well-known image processing technology such as threshold decision, a region growing method or the like is utilized. For example, FIG. 7 is a diagram showing a result that the large FOV image of the subject 6 on the left side in the drawing has been subjected to threshold decision with air on the right side in the drawing. In a case where a threshold value TH=−950 [HU] is set manually or automatically, an under-TH one is discriminated as a region 191 of air and an over-TH one is as a region 192 other than air. In addition to the above, a method of combining prior information such as shape information, position information and the like of the selected processing object with the region growing method can be given. Thus, a boundary between the processing object and a region other than that can be extracted and the regions can be discriminated. Although in the present embodiment, air has been set as the processing object by way of example, the part, the tissue or the like as shown in the processing object list 144 in FIG. 3 may be discriminated as the processing object.

Next, the smoothing function 156 which is the cause elimination unit in the processing flow example in FIG. 5 eliminates a false image of the large FOV image by applying the general smoothing such as, for example, a moving average filter of D [pixels]×D [pixels], a convolution operation using a Gaussian function or the like in step 173 in FIG. 6. Although in the present embodiment, the moving average filter of D=3 has been used assuming the square regions, it is similarly applicable to an arbitrary region such as a circular, rectangular, cubic, rectangular parallelepiped, or spherical one not limited to the square one.

Although in the present embodiment, the cause elimination unit has been implemented by applying smoothing to the processing object, in a case where the CT values of air, the bed and the like are known, the cause elimination unit may be implemented by replacing the pixel value of the processing object with the known CT value. For example, air is −1000 [HU] and the bed is −200 [HU]. Thus, the cause elimination unit which can eliminate the false image with high accuracy in comparison with smoothing can be configured.

Next, the background image creation function 157 replaces the small FOV region in the large FOV region with the CT value −1000 [HU] of air on the basis of the input reconstruction range 143 in step 174. Thus, a background image that a CT value which is different from the CT value of air is present is created in the background region other than the small FOV.

This background image creation function 157 corresponds to the background image creation unit which creates the background image by dividing the above-mentioned corrected CT image into the local region and the background region other than that and replacing the pixel value of the local region with an X-ray absorption rate of a fixed value.

Although in the present embodiment, processing has been executed in order of the processing object discrimination function 155, the smoothing function 156 for cause elimination, and the background image creation function 157, the same advantage can be also obtained by calculating in order of the background image creation function 157, the processing object discrimination function 155, and the smoothing function 156 which is the cause elimination function, not limited to the present embodiment. In this case, since the background region can be extracted by the background image creation function 157, calculation of discrimination and cause elimination such as smoothing or the like of the processing object in the local region can be omitted and calculation of smoothing or the like can be performed only on the CT image of the background region in the CT image obtained from the measurement projection data, so that the calculation amount can be reduced.

Next, the forward projection function 158 forward projects the background image $\lambda^{k=0}(j)$ to obtain background projection data $RC^k(i)$ as expressed in Formula 1 in step 175.

[Numerical Formula 1]

$$RC^k(i) = \sum_{j=1}^{J} (p(i,j) \cdot \lambda^k(j))$$ (Formula 1)

However, $$\sum_{i=1}^{j} p(i,j) = 1$$

This forward projection function 158 functions as the background projection data calculation unit for calculating the projection data as the integrated value of the background image on the path connecting the above-mentioned X-ray generation unit and X-ray detection unit.

Next, the data comparison function 159 subtracts the background projection data from the measurement projection data as expressed to obtain local measurement projection data $R_r^k(i)$ as expressed in Formula 2 in step 176.

[Numerical Formula 2]

$$R_r^k(i) = R(i) - RC^k(i)$$ (Formula 2)

This data comparison function 159 functions as the local measurement projection data calculation unit for subtracting the background projection data from the above-mentioned measurement projection data to calculate the measurement projection data of the local region.

Next, the small FOV image calculation function 153 in FIG. 4 will be described. As shown in FIG. 5, the small FOV image calculation function 153 is implemented by an analytical reconstruction function 160, a forward projection function 161, a data comparison function 162, a back projection process function 163, and an image update function 164. First, for the local measurement projection data $Rr^k(i)$ obtained by the data comparison function 159, the analytical reconstruction function 160 calculates a small FOV image $\lambda_r^{k=0}(j)$ indicating the CT value of the subject using the well-known analytical reconstruction method such as the Feldkamp method or the like in step 177. Although in the present embodiment, the small FOV image has been calculated from the obtained local measurement projection data $Rr^k(i)$, the small FOV image may be calculated using the measurement projection data $R(i)$.

This analytical reconstruction function 160 functions as the local image calculation unit for calculating the CT image of the local region which is the X-ray absorption rate distribution from the above-mentioned local measurement projection data.

Next, it iteratively corrects the obtained small FOV image which is the CT image of the local region as an initial image of the iterative reconstruction method. If the updating number k in calculation is smaller than a set updating number K in step 178, it will correct the image using the local measurement projection data $R_r(i)$ in steps 179 to 182.

As an algorithm for correcting the image, for example, ASIRT (Additional simultaneous reconstruction technique) which is one of the iterative reconstruction methods is expressed by Formula 3.

[Numerical Formula 3]

$$\lambda_r^{k+i}(j) = \lambda_r^k(j) + \alpha \cdot \sum_{i=1}^{I} \left\{ \frac{(R_r(i) - R_r C^k(i)) \cdot p(i,j)}{\sum_{j=1}^{J} p(i,j)} \right\} \quad \text{(Formula 3)}$$

$Rr^k(i)$ indicates the pixel value of the pixel j of the small FOV image in the updating number k in calculation and is assumed to be configured by J pixels. The small FOV image is applicable not only to the general two-dimensional (the x, y directions) tomographic image but also to the one-dimensional data (the x direction), the three-dimensional data (the x, y, z directions) that the images are superimposed in the anteroposterior direction z, or even the four-dimensional data (the x, y, z, t directions) that the time direction is taken into account in three-dimension. $R_r C^k(i)$ indicates the calculation projection data obtained by forward projecting the small FOV image in the updating number k. In addition, a relaxation coefficient α indicates a rate of correction to the pixel value $\lambda_r^k(j)$ of the updating number k.

Next, the forward projection function 161 forward projects $\lambda_r^k(j)$ expressed in Formula 4 to obtain the calculation projection data $R_r C^k(i)$ of the local region in step 179.

[Numerical Formula 4]

$$R_r C^k(i) = \sum_{j=1}^{J} (p(i,j) \cdot \lambda_r^k(j)) \quad \text{\{Formula 4\}}$$

However, $$\sum_{i=1}^{I} p(i,j) = 1$$

This forward projection function 161 functions as the local projection data calculation unit for calculating the local projection data as the integrated value of the local CT image on the path connecting the above-mentioned X-ray generation unit and X-ray detection unit.

Next, the data comparison function 162 comparatively calculates the local calculation projection data $R_r C^k(i)$ and the local measurement projection data $Rr^k(i)$ to obtain local updated projection data $\Delta R_r^k(i)$ as expressed in Formula 5 in step 180.

[Numerical Formula 5]

$$\Delta R_r^k(i) = R_r(i) - R_r C^k(i) \quad \text{(Formula 5)}$$

Next, the back projection process function 163 performs back projection process on the local updated projection data $\Delta R_r^k(i)$ to obtain an updated image $\Delta \lambda_r^k(j)$ as expressed in Formula 6 in step 181.

[Numerical Formula 6]

$$\Delta \lambda_r^k(j) = \sum_{i=1}^{I} \left\{ \frac{\Delta R_r^k(i) \cdot p(i,j)}{\sum_{j=1}^{J} p(i,j)} \right\} \quad \text{\{Formula 6\}}$$

Next, the image update function 164 obtains a small FOV image $\lambda_r^{k+1}(j)$ corrected using the updated image $\Delta \lambda_r^k(j)$ as expressed in Formula 7 in step 182. By way of example, assuming that α=1.0 is set, the relaxation coefficient α which is at least 1.0 is used for fast convergence and the one which is less than 1.0 is used for slow convergence.

[Numerical Formula 7]

$$\lambda_r^{k+1}(j) = \lambda_r^k(j) + \alpha \cdot \Delta \lambda_r^k(j) \quad \text{(Formula 7)}$$

The local image correction unit for iteratively correcting the local CT image such that the above-mentioned local calculation projection data becomes equal to the local measurement projection data is configured by these data comparison function 162, back projection process function 163, and image update function 164.

As described above, at the completion of steps 179 to 182 in FIG. 6, the updating number k is incremented to k+1 in step 183, and looping is performed by returning to step 178. At that time, when the incremented updating number k is larger than the set updating number K, updating is terminated and the image display unit 137 displays and outputs the obtained CT image in step 184.

As described above, one example of the calculation procedure of the iterative reconstruction method in the embodiment 1 has been shown in steps 178 to 184 in FIG. 6. The iterative reconstruction method expressed by Formula 3 in the embodiment 1 is merely one example and it may be applied to other methods such as well-known SPS, OS-SPS, PWLS, OS-PWLS, MSIRT, GRADY, CONGR, ART, SART, ML-EM, OS-EM, FIRA, RAMLA, DRAMA and the like.

Finally, in the image display unit 137 in FIG. 2, the calculated CT image is displayed on the monitor 123 to provide the operator with information. Incidentally, it is also possible to connect with external terminals over a network such as a local area network, a telephone line, Internet or the like using a network adopter to transmit and receive the CT image between it and these terminals.

In the present invention, the large FOV image can be repetitively corrected using the iterative reconstruction method in the large FOV calculation function 151. Thus, errors caused by the false image and noise of the large FOV image can be reduced to prevent deterioration of the CT value accuracy of the small FOV image.

In the present embodiment, the processing object discrimination function 155 discriminates the processing object from the large FOV image. Thus, highly accurate discrimination processing can be performed by utilizing the CT value at each position of the image. For example, known shape information on the bed or the like is introduced in advance into discrimination processing to promote accuracy improvement.

Although in the present embodiment, the CT image has been reconstructed using the measurement projection data obtained from the one rotation, it is also applicable to well-known half reconstruction not limited to one rotation. At that time, it is assumed that a perfect measuring region is a region that an angle of rotation which satisfies perfect acquisition conditions has been obtained in the half reconstruction.

In addition, although in the present embodiment, a normal scanning system has been supposed, it goes without saying that the present invention may be applied also to a step and shoot system that operation and stop of the table 5 are repeated in this order at a fixed interval to perform a normal scan, or a helical scan system that imaging is performed while moving the table.

Embodiment 2

Next, as a second embodiment, a configuration for implementing an X-ray CT device loaded with iterative reconstruction software that part of the embodiment 1 has been changed will be described. In the following, only essential parts of the X-ray CT device of the embodiment 2 will be described with reference to the drawings. Since other configurations are the same as the configurations of the X-ray CT device described in the embodiment 1, description thereof is omitted here. However, it is different from the first embodiment in that it is of a configuration that the background projection data calculation unit of the image generation unit of the second embodiment is equipped with the cause elimination unit for eliminating the cause to deteriorate the calculation accuracy of the background projection data.

Figure 8:
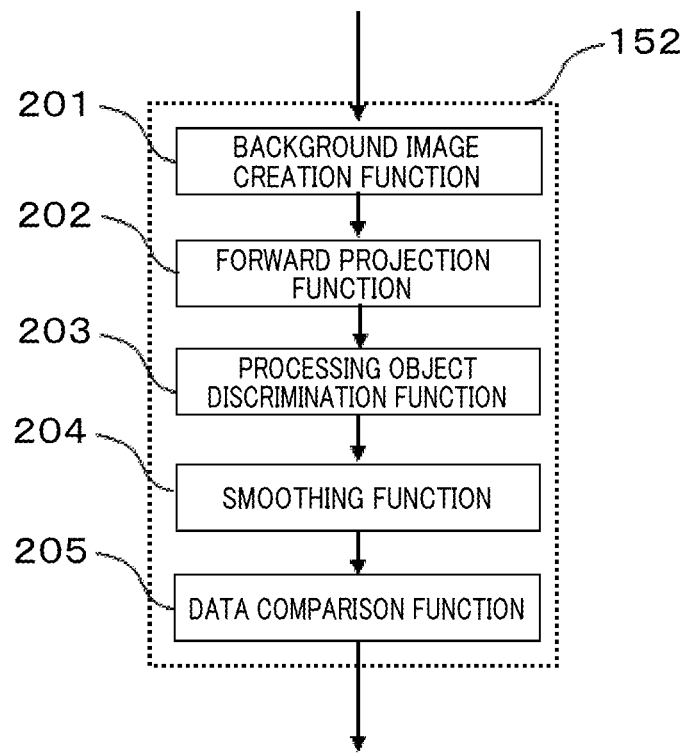
FIG. 8 is a diagram for explaining respective functions of a reconstruction processing unit in an embodiment 2.

FIG. 8 is the one that the local measurement projection data calculation function 152 in the reconstruction processing unit 136 shown in FIG. 4 and FIG. 5 which has been described in the embodiment 1 has been partially changed. In the local measurement projection data calculation function 152 of the present embodiment, processing is executed in order of a background image creation function 201 for creating a background image, a forward projection function 202 for forward projecting and calculating the background image, a processing object discrimination function 203 for discriminating the object for smoothing from the forward projected background projection data, a smoothing function 204 which functions as the cause elimination unit for smoothing the background projection data, and a data comparison function 205 for subtracting the background projection data from the measurement projection data. In the present embodiment, the CT values are adjusted such that air will be 0 [HU], the bed will be 200 [HU], and water will be 1000 [HU].

As shown in FIG. 8, first, the background image creation function 201 replaces the region of the small FOV in the large FOV image with the CT value 0 [HU] of air on the basis of an input reconstruction range 143.

Next, the forward projection function 202 forward projects the background image $\lambda^{k=0}(j)$ expressed in Formula 1 to obtain background projection data $RC^k(i)$.

[Numerical Formula 8]

$$RC^k(i) = \sum_{j=1}^{J} (p(i, j) \cdot \lambda^k(j))$$ (Formula 1)

However, $$\sum_{i=1}^{j} p(i, j) = 1$$

Next, the processing object discrimination function 203 discriminates the object which has been selected in the processing object list 144 from the background projection data. Since in the present embodiment, air is selected, air and the region other than air are discriminated. As a discrimination method, a well-known image processing technique such as threshold value discrimination, a region growing method or the like is utilized. For example, one example of background projection data 193 at a projection angle=45 degrees is shown in FIG. 9.

Figure 9:
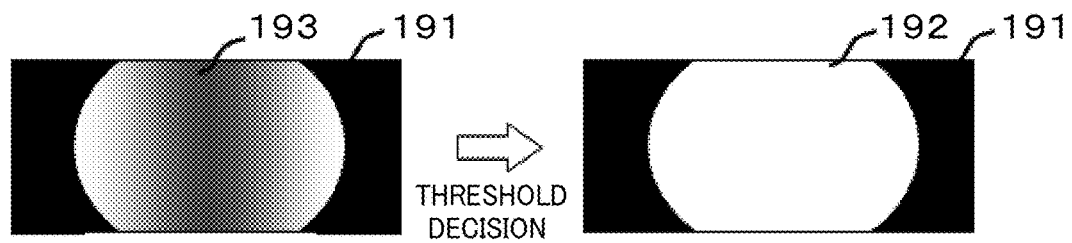
FIG. 9 is a diagram for explaining discrimination of a processing object by threshold decision in the embodiment 2.

The coordinate in a longitudinal direction in FIG. 9 is a detector row number and the coordinate in a transverse direction is a channel number. For example, the number of rows is 64. As shown in FIG. 9, in a case where the threshold value TH=100 [HU] is set manually or automatically, the under-TH one is discriminated as the air region 191 and the over-TH one is as the region 192 other than air.

In addition to the above, the method of combining the prior information such as the shape information, the position information and the like of the selected processing object with the region expansion method can be given. Thus, the boundary between the processing object and the region other than that can be extracted and the regions can be discriminated. Although in the present embodiment, air has been set as the processing object by way of example, the part, the tissue or the like may be discriminated as the processing object.

In the present embodiment, as shown in FIG. 8, the processing object discrimination function 203 discriminates the processing object from the background projection data obtained by the background image creation function 201 and the forward projection function 202. Since the background projection data utilizes the integrated value of the CT value at each position, a difference between the processing object and a not-objected one becomes large and discrimination can be performed highly accurately. For example, in case of air and water, when discriminating the processing object from the image, the difference in CT value amounts to about 1000 [HU]. On the other hand, when discriminating the processing object from the background projection data in the processing object discrimination function 203 as in the present embodiment, the difference in CT value amounts to about 1000×a permeation length of water [HU] and it is seen that highly accurate discrimination can be performed by utilizing the large difference.

Embodiment 3

In the present embodiment, a configuration for implementing an X-ray CT device loaded with iterative reconstruction software that part of the embodiments 1 and 2 has been changed will be described. In the X-ray CT device of the present embodiment, a CT image to be calculated is divided into the local region and the background region other than that and only the CT image of the background region which is the X-ray absorption rate distribution is calculated from the measurement projection data in the large FOV image calculation function 151 of the reconstruction processing unit 136 shown in FIG. 4 and FIG. 5 of the embodiment 1.

That is, the X-ray CT device of the present embodiment is equipped with the X-ray generation unit for generating the X-ray, the X-ray detection unit for detecting the X ray after transmitted through the subject, the projection data calculation unit for generating the measurement projection data from the detection signal of the X-ray detection unit which has been measured by rotating the X-ray generation unit and the X-ray detection unit, and the image generation unit for generating the CT image from the measurement projection data, and is different from the first and second embodiments in that this image generation unit is equipped with a background image creation unit for dividing the CT image to be calculated into the local region and the background region other than that and creating the CT image of the background region which is the X-ray absorption rate distribution directly from the measurement projection data.

Figure 10:
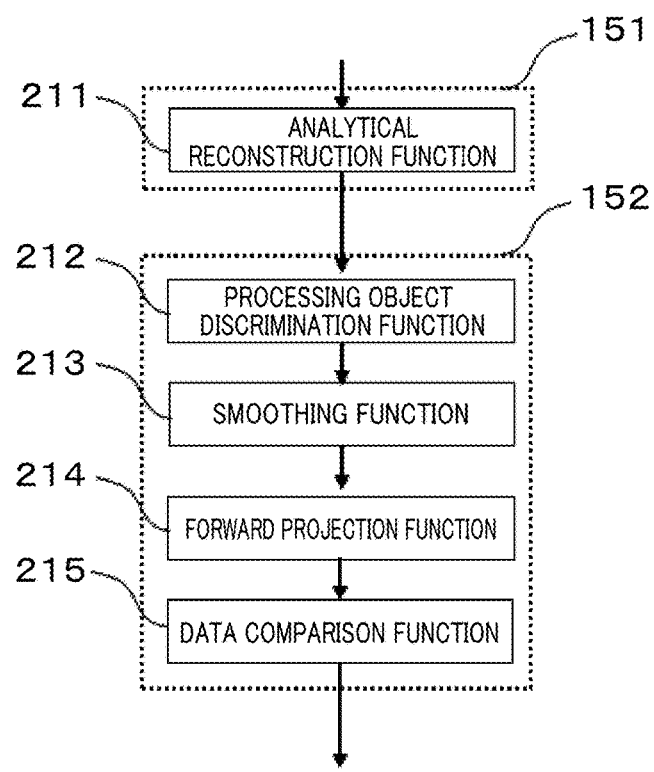
FIG. 10 is a diagram for explaining respective functions of a reconstruction processing unit in an embodiment 3.

In the following, essential parts of the embodiment 3 will be described with reference to FIG. 10. Since other configurations are the same as the configurations of the embodiments 1 and 2 which have been described in detail previously, description thereof is omitted here. FIG. 10 is a diagram for explaining a function of the reconstruction processing unit 136 that the large FOV image calculation function 151 and the local measurement projection data calculation function 152 shown in FIG. 4 and FIG. 5 have been partially changed.

In the present embodiment, the large FOV image calculation function 151 is implemented by an analytical reconstruction function 211 for reconstructing only the background region of the large FOV image as mention0 above. Thus, the local measurement projection data calculation function 152 of the reconstruction processing unit 136 can be implemented by executing processing in order of a processing object discrimination function 212 for discriminating the object for smoothing from the obtained background image, a smoothing function 213 for smoothing the background image, a forward projection function 214 for forward projecting and calculating the background image, and a data comparison function 205 for subtracting the background projection data from the measurement projection data.

In the present embodiment, a reconstruction arithmetic operation of the large FOV image in the local region can be omitted in comparison with the embodiment 1 or the embodiment 2 by using the image calculation unit for dividing the CT image to be calculated into the local region and the background region other than that and calculating the CT image of the background region which is the X-ray absorption rate distribution from the measurement projection data as the analytical reconstruction function 211. Thus, since calculations for discrimination, smoothing and forward projection process of the processing object coming after the reconstruction arithmetic operation can be omitted, the calculation amount can be reduced.

Embodiment 4

In the present embodiment, another configuration of the X-ray CT device loaded with the iterative reconstruction software loaded will be described. In the following, only essential parts of the X-ray CT device of the embodiment 4 will be described with reference to the drawing. Since other configurations are the same as the configurations of the X-ray CT device described in the embodiment 1, description thereof is omitted here.

Figure 11:
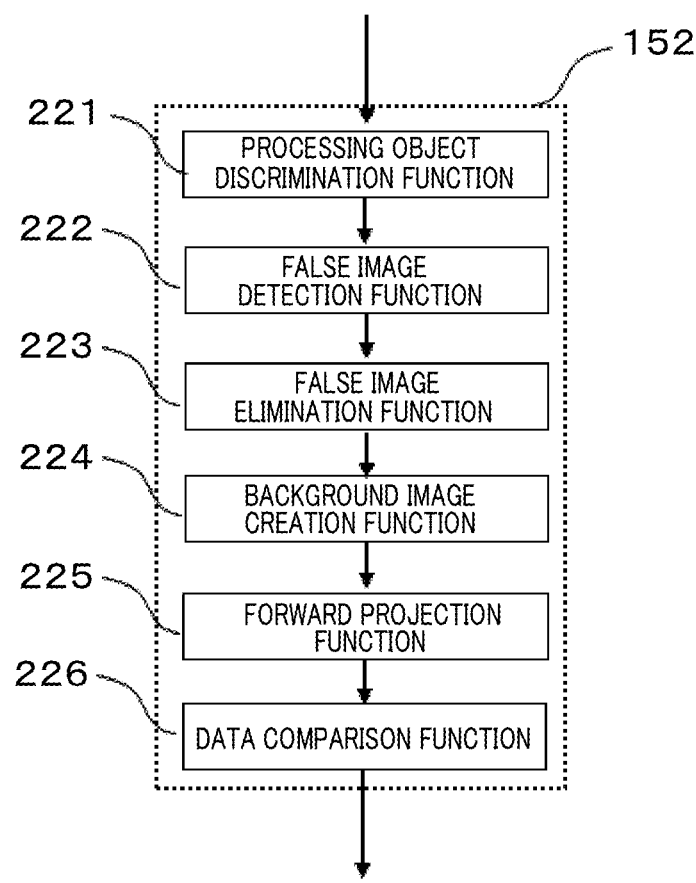
FIG. 11 is a diagram for explaining respective functions of a reconstruction processing unit in an embodiment 4.

FIG. 11 shows functions of a reconstruction processing unit in the embodiment 4 that the local measurement projection data calculation function 152 shown in FIG. 4 and FIG. 5 of the embodiment 1 has been partially changed.

In the local measurement projection data calculation function 152 of the present embodiment, processing is executed in order of a processing object discrimination function 221 for discriminating the object for a cause elimination function from the large FOV image, a false image detection function 222 for detecting a false image from a discriminated region, a false image elimination function 223 which functions as the cause elimination unit for eliminating the detected false image, a background image creation function 224 for creating a background image, a forward projection function 225 for forward projecting and calculating the background image, and a data comparison function 226 for subtracting the background projection data from the measurement projection data.

First, the processing object discrimination function 221 discriminates the object selected by the processing object list 144 from the large FOV image similarly to the embodiment 1. Since air is selected also in the present embodiment, air and the region other than air are discriminated.

Next, the false image detection function 222 detects the false image such as a streak artifact or the like from the region of the discriminated processing object. As a detection method, a well-known image processing technique such as threshold decision or the like is utilized. In a case where an upper limit threshold value THU=−950 [HU] and a lower limit threshold value THL=−1050 [HU] are set manually or automatically, a CT value in the discriminated region which is less than THU and at least THL is discriminated as the air region 191 and the one other than that is as the false image.

In the following, the background image creation function 224, the forward projection function 225, and the data comparison function 226 are the same as those in the embodiment 1. Although in the present embodiment, discrimination of the processing object has been performed, it is not limited to the present embodiment, and in a case of omitting the processing object discrimination function, the calculation amount can be reduced.

A simulation experiment was performed under the condition that quantum noise is not taken into account in order to verify the effectiveness of the present embodiment. A phantom to be imaged was set by supposing the elliptical human abdomen. The phantom of the human abdomen forms a structure having a CT value which approximates that of a biological tissue.

Figure 12:
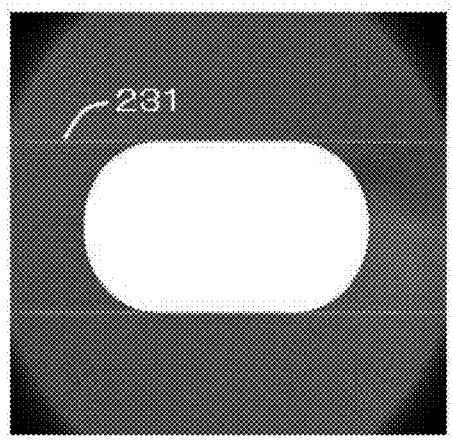
FIG. 12 is a diagram for explaining a phantom used in simulation and advantages in the embodiment 4.
Figure 12:
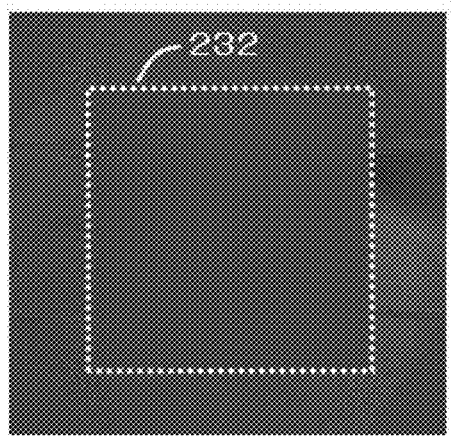
Figure 12:
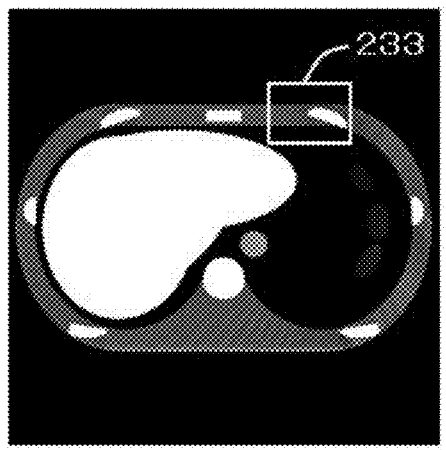
Figure 12:
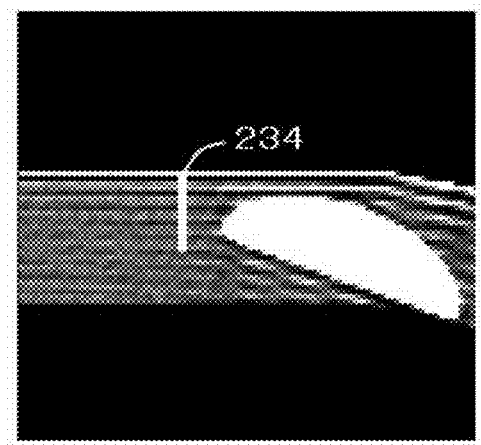
Figure 12:
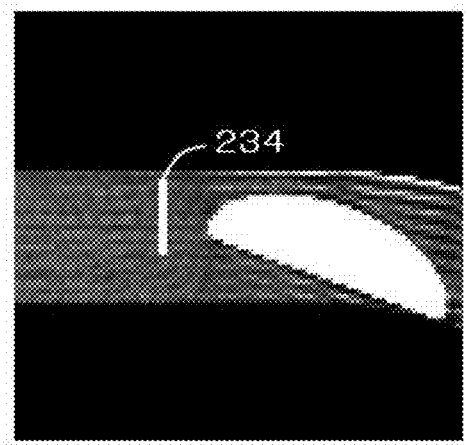

Results of simulation are shown in FIG. 12 (a) to FIG. 12 (e). FIG. 12 (a) is a large FOV image which has been reconstructed with the large FOV=700 [mm]. First, the region of air was discriminated from the large FOV image as the processing object and a false image 231 was discriminated from the discriminated region and eliminated. Threshold values used in discrimination of the false image 231 are THU=−950 [HU], and THL=−1050 [HU]. FIG. 12 (b) is an image that a small FOV 232 in the large FOV image was set to 450 [mm] and the inside of the small FOV was replaced with −1000 [HU]. FIG. 12 (a) and FIG. 12 (b) are assumed that a window level (hereinafter, WL)=−1000 [HU], and a window width (hereinafter, referred to as WW)=100 [HU].

Next, the small FOV image which has been reconstructed with the small FOV=450 [mm] on the basis of the local measurement projection data calculated from the image shown in FIG. 12 (b) is shown in FIG. 12 (c). FIG. 12 (d) is an enlarged diagram of the small FOV image by a conventional method and FIG. 12 (e) shows an enlarged diagram of the small FOV image by the embodiment 4. An enlarged region 233 is displayed in FIG. 12 (c). FIGS. 12 (c), (d) and (e) are images of the updating number=5 times, the subset number=14, and the relaxation coefficient $\alpha$=1.0, subjected to image reconstruction by ASIRT using a well-known subset method. FIGS. 12 (c), (d) and (e) are assumed that WL=50 [HU], and WW=20 [HU].

Figure 13:
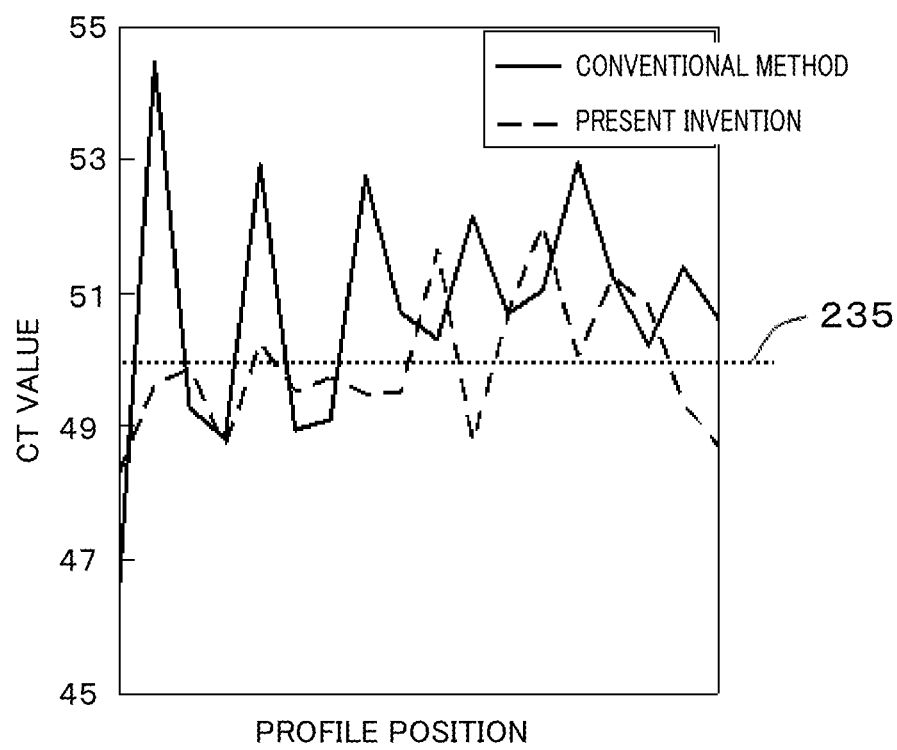
FIG. 13 is a diagram for explaining the advantages in the embodiment 4.

As a result of evaluation, while in the conventional method in FIG. 12 (d), increase and decrease of the CT value are observed in a transverse direction of the subject, the influence of the increase and decrease of the CT value could be suppressed by the embodiment 4 in FIG. 12 (e). A result of measurement of a profile 234 shown in FIGS. 12 (d) and (e) is shown in FIG. 13 as quantitative evaluation. The vertical axis shows the CT value and the horizontal axis shows the profile position. A downward direction of the profile position on the image in FIG. 12 (d) or (e) matches a rightward direction of the horizontal axis in FIG. 13. From the result in FIG. 13, it is found that the CT value accuracy has been improved, from that the invention pertaining to the embodiment 4 approaches a true value 235 shown by a dotted line in comparison with the conventional method.

In the present embodiment, the processing object discrimination function 221 discriminates the processing object for the cause elimination unit from the large FOV image. Thus, highly accurate discrimination processing can be performed by utilizing the CT value at each position of the image. For example, accuracy improvement is promoted by introducing in advance known shape information of the bed or the like into the discrimination processing. Next, the false image detection function 222 can perform highly accurate discrimination processing by discriminating the processing object from the large FOV image utilizing the CT value at each position of the image. For example, since a streak artifact can be concluded as linear noise, it can be discriminated by utilizing the shape information.

Although the processing object discrimination function 221 of the present embodiment has discriminated the processing object from the large FOV image, the processing object can be discriminated from the background projection data similarly to the embodiment 2. The false image detection function 222 in FIG. 11 can discriminate the false image with high accuracy by discriminating the processing object from the background projection data. For example, a difference in integrated value between the processing object and the other becomes remarkable by integrating the streak artifact linearly and discrimination is facilitated. Deterioration of the CT value accuracy by the false image or the like can be prevented by performing smoothing by filtering on the discriminated false image, or by replacing the pixel value of the false image part with the X-ray absorption rate of the fixed value.

Embodiment 5

In the present embodiment, a further configuration of the X-ray CT device in which part of the embodiments 1 and 2 has been changed and which is loaded with the iterative reconstruction software will be described. In the following, only essential parts of the X-ray CT device of the embodiment 5 will be described with reference to the drawing. Since other configurations are the same as the configurations of the X-ray CT device described in the embodiment 1, description thereof is omitted here.

Figure 14:
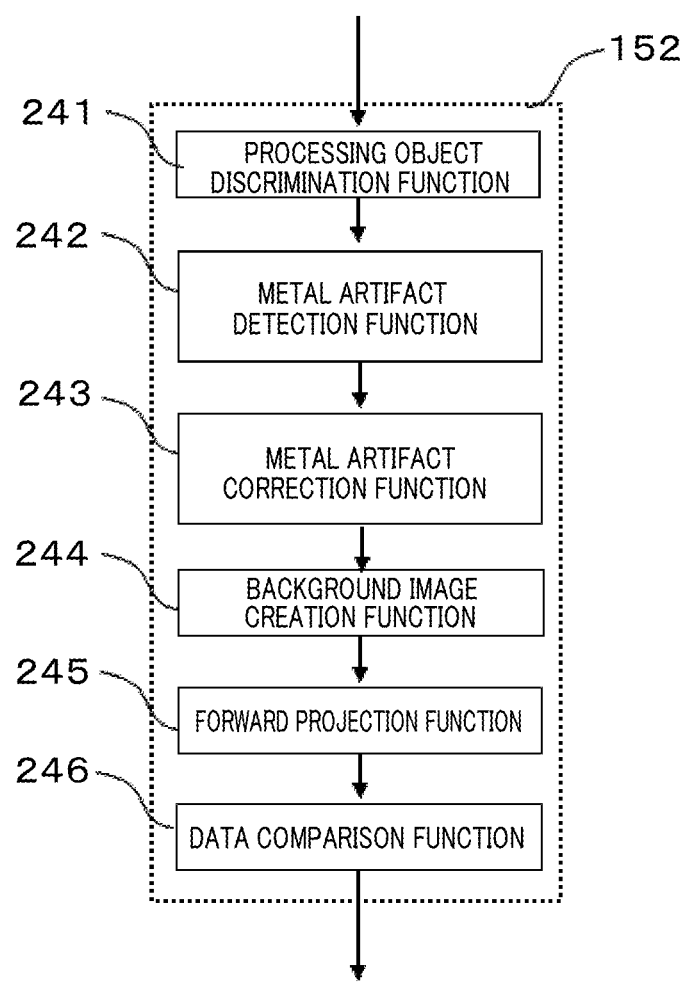
FIG. 14 is a diagram for explaining respective functions of a reconstruction processing unit in an embodiment 5.

FIG. 14 is the one that the local measurement projection data calculation function 152 of the reconstruction processing unit 136 shown in FIG. 4 and FIG. 5 has been partially changed.

In the present embodiment, processing is executed in order of a processing object discrimination function 241 for discriminating the object on which metal artifact correction is to be performed, a metal artifact detection function 242 for detecting a metal artifact from the discriminated processing object, a metal artifact correction function 243 which functions as the cause elimination unit for correcting the detected metal artifact, a background image creation function 244 for creating a background image, a forward projection function 245 for forward projecting and calculating the background image, and a data comparison function 246 for subtracting the background projection data from the measurement projection data.

First, the processing object discrimination function 241 discriminates the object selected by the processing object list 144 from the large FOV image similarly to the embodiment 1. Since air is selected also in the present embodiment, air and the region other than air are discriminated.

Then, the metal artifact detection function 242 uses a well-known image processing technique such as threshold value discrimination or the like. For example, in a case where the threshold value TH=2000 [HU] is set manually or automatically in the threshold value discrimination, the over-TH one in the discriminated region is discriminated as the region of metal.

Next, the metal artifact correction function 243 which is the cause elimination function forward projects and calculates the discriminated region of metal and presumes a channel that the metal artifact is included on the measurement projection data. Next, the influence of the metal artifact can be reduced by interpolation from integrated values of the CT values of a plurality of channels adjacent to the presumed channel. In the following, the background image creation function 244, the forward projection function 245 and the data comparison functions 246 are the same as those in the embodiment 1.

Embodiment 6

In the present embodiment, a further configuration of the X-ray CT device in which part of the embodiments 1 and 2 has been changed and which is loaded with the iterative reconstruction software will be described. In the following, only essential parts of the X-ray CT device of the embodiment 6 will be described with reference to the drawing. Since other configurations are the same as the configurations of the X-ray CT device described in the embodiment 1, description thereof is omitted here.

Figure 15:
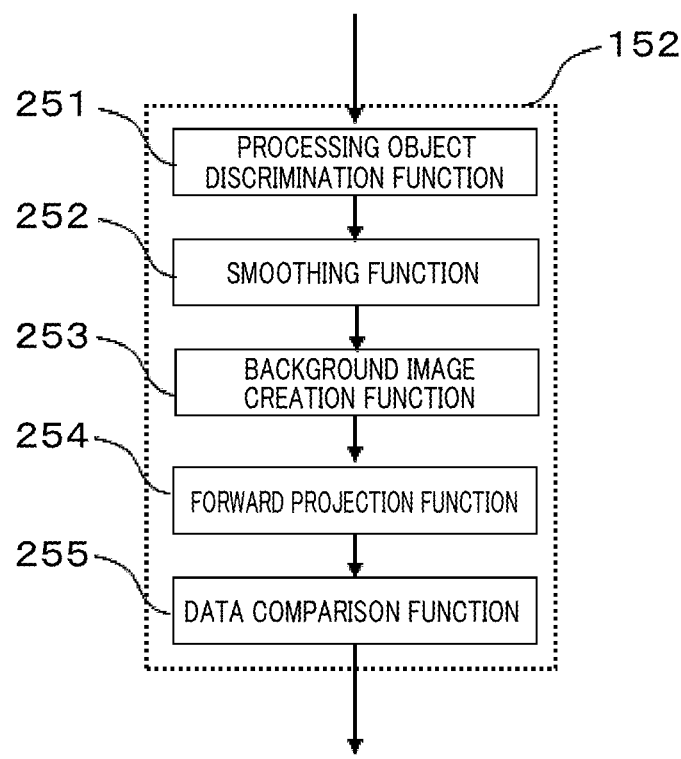
FIG. 15 is a diagram for explaining respective functions of a reconstruction processing unit in an embodiment 6.

FIG. 15 is the one that the local measurement projection data calculation function 152 of the reconstruction processing unit 136 shown in FIG. 4 and FIG. 5 has been partially changed.

In the local measurement projection data calculation function 152 of the present invention, processing is executed in order of a processing object discrimination function 251 for discriminating the object to be corrected for an quantization error, a smoothing function 252 which is the cause elimination unit for smoothing the discriminated processing object, a background image creation function 253 for creating a background image, a forward projection function 254 for forward projecting and calculating the background image, and a data comparison function 255 for subtracting the background projection data from the measurement projection data.

Figure 16:
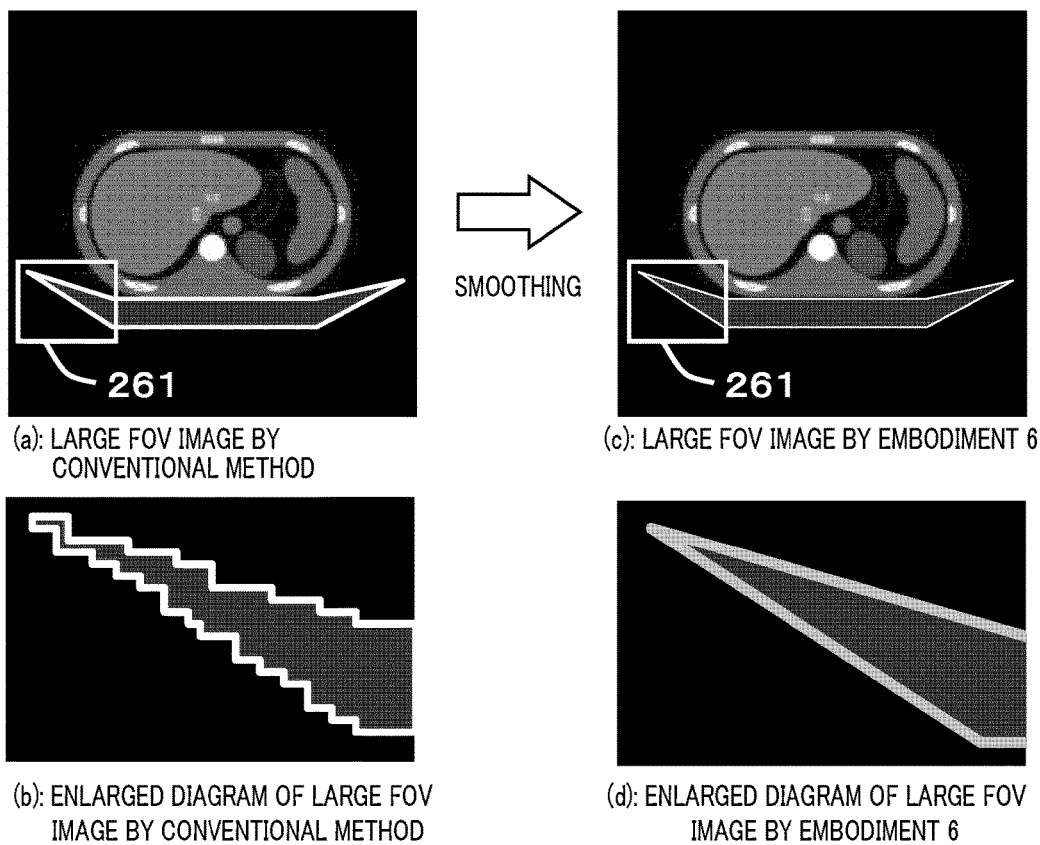
FIG. 16 is a conceptual diagram for explaining the advantages in the embodiment 6.

The influence of the error by quantization is increased as an image of larger size [mm/pixel] of one pixel and of lower resolution is obtained. As a condition that the error is large, for example, a place where a difference in CT value is large such as a boundary part between the bed and air, a boundary part between a bone and the fat or the like may be given. FIG. 16 (a) is a large FOV image of the subject 6 by a conventional method, FIG. 16 (b) is a diagram that a region 261 of the bed and air has been enlarged. By FIG. 16 (b), the bed surface of a linear shape is imaged as a stepped shape under the influence of the quantization error on the boundary part between a bed end part and air. In order to solve this problem, in the present embodiment, a region which has been discriminated by the processing object discrimination function 251 and is large in influence of the quantization error is smoothed to reduce the influence of the quantization error.

FIG. 16 (c) is a large FOV image of the subject by the present embodiment, and FIG. 16 (d) is a diagram that the region 261 of the bed and air has been enlarged. As shown in FIG. 16 (d), it is seen that the bed surface approaches to the linear shape in comparison with the conventional method by the effect of smoothing.

Next, the local measurement projection data calculation function 152 will be described in detail. In the processing object discrimination function 251 of the present embodiment, in respective pixels of the large FOV image, a pixel that a difference in CT value with its adjacent pixel is larger than the threshold value [HU] is detected. At that time, an absolute value is used for the difference in CT value and for example, it is assumed that TH=500 [HU]. In the present embodiment, the adjacent pixel is not limited to a pixel which is in adjacently contact with a target object and the pixel may be determined within an arbitrary range.

Next, in the smoothing function 252 implementing the cause elimination function, the discriminated processing object, a well-known smoothing process such as, for example, a moving average filter of D [pixels]×D [pixels], a convolution operation using a Gaussian function or the like is applied to reduce the influence of the quantization error in the large FOV image. Although in the present embodiment, the moving average filter of D=3 has been used supposing the square region, it is not limited to the square and the present invention can be similarly applied to arbitrary regions such as circular, rectangular, cubic, rectangular parallelepiped, spherical and other ones.

Although in the present embodiment, the moving average filter not depending on the CT value and the direction has been applied, it is not limited to the present embodiment. For example, a condition that the smoothing effect with the adjacent pixel is increased as the difference in CT value is increased is set. Thus, in a case where the difference in CT value is large and the influence of the quantization error is large, high reduction effect can be expected. To the contrary, in a case where the difference in CT value of a boundary part or the like between tissues is small and the influence of the quantization error is small, deterioration of the CT value accuracy by smoothing can be prevented.

In the present embodiment, the processing object discrimination function 251 discriminates the processing object from the large FOV image. Thus, highly accurate discrimination processing can be performed by utilizing the CT value at each position of the image. For example, known shape information on the bed or the like is introduced in advance into the discrimination processing, thereby promoting accuracy improvement.

Although the processing object discrimination function 251 of the present embodiment has discriminated the processing object from the large FOV image, the processing object can be discriminated from the background projection data similarly to the embodiment 2. Since the background projection data is calculated by utilizing the integrated value of the CT value at each position, the difference between the processing object and a not-objected one is increased and discrimination processing can be performed with high accuracy. For example, in case of air and water, if the processing object is discriminated from the image, the difference in CT value will amount to about 1000 [HU]. On the other hand, if the processing object is discriminated from the background projection data, the difference in CT value will amount to about 1000×water permeation length [HU] and it is seen that the difference is increased.

Embodiment 7

In the present embodiment, another configuration for implementing the X-ray CT device in which part of the embodiment 6 has been changed and which is loaded with the iterative reconstruction software will be described. In the following, the X-ray CT device of the embodiment 7 will be described with reference to the drawing.

Figure 17:
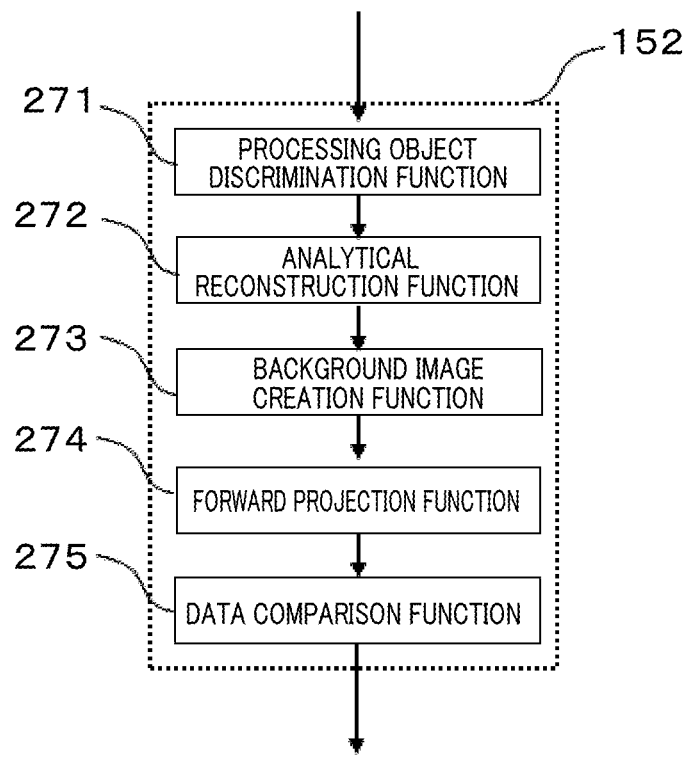
FIG. 17 is a diagram for explaining respective functions of a reconstruction processing unit in an embodiment 7.

FIG. 17 shows a local measurement projection data calculation function 152 of the present embodiment that the local measurement projection data calculation function 152 shown in FIG. 4 and FIG. 5 has been partially changed. In the local measurement projection data calculation function 152 of the present embodiment, processing is executed in order of a processing object discrimination function 271 for discriminating the object to be corrected for quantization error, an analytical reconstruction function 272 for re-calculating the discriminated processing object with high resolution, a background image creation function 273 for creating a background image, a forward projection function 274 for forward projecting and calculating the background image, and a data comparison function 275 for subtracting the background projection data from the measurement projection data.

In the processing object discrimination function 271, a region which is large in quantization error is discriminated as the processing object on the basis of a difference in CT value with its adjacent pixel similarly to the embodiment 6.

Figure 18:
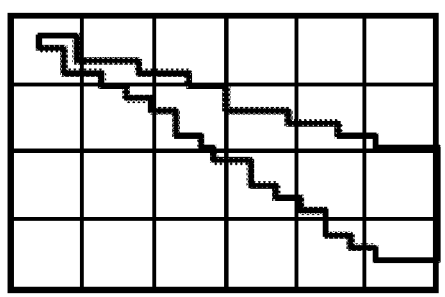
FIG. 18 is a conceptual diagram for explaining the advantages in the embodiment 7.
Figure 18:
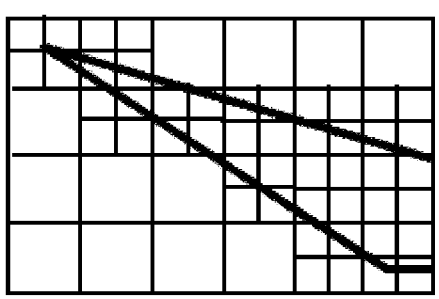

Next, in the analytical reconstruction function 272 acting as the cause elimination unit, targeting on the discriminated region which is large in quantization error, a large FOV image $\lambda^{k=0}(j)$ indicating the CT value of the subject is re-calculated using the well-known analytical reconstruction method such as the Feldkamp method or the like. At that time, the influence of the quantization error can be reduced by making the pixel size of the CT image smaller than a conventional set value to increase the resolution. For example, FIG. 18 (*a*) shows an image that the bed has been enlarged similarly to FIG. 16, and in the present embodiment in FIG. 18 (*b*) that it is divided with uniform pixels, limiting to the pixels where the bed which is large in quantization error is present, reconstruction is performed by making the pixel size smaller to increase the resolution. In the present embodiment, an example that the resolution has been increased two times higher than the conventional set value is shown.

Thus, since the influence of the quantization error can be reduced without increasing the resolution of the entire region of the large FOV image, deterioration of the CT value accuracy can be prevented by slightly increasing the calculation amount.

Although various embodiments of the present invention have been described hereinabove, the present invention is not limited to the above-mentioned embodiments and various modified examples are included. For example, the above-mentioned embodiments have been described in detail for better understanding of the present invention and they are not always limited to those having all the configurations which have been described.

In addition, it is possible to replace part of a configuration of a certain embodiment with a configuration of another embodiment, and it is also possible to add a configuration of another embodiment to a configuration of a certain embodiment. In addition, with respect to part of a configuration of each embodiment, addition, elimination and replacement of another configuration are possible.

Further, although part or all of the above-mentioned respective configurations, functions, processing units and the like may be implemented by software by creating the above-mentioned program, part or all of them may be implemented by hardware, for example, by designing them by an integrated circuit or the like.

Still further, although each embodiment has been described as the X-ray CT device for living bodies, it goes without saying that the present invention may be applied to an X-ray CT device targeting on nondestructive inspections such as explosive inspections, product inspections and the like. In addition, although each embodiment has shown a well-known third-generation multi-slice X-ray CT device by way of example, the present invention can be also applied to well-known first-, second-, and fourth-generation X-ray CT devices and can be further applied to well-known single-slice X-ray CT devices and electron beam CTs.

In the present specification which has been described in detail hereinabove, various inventions are disclosed in addition to the invention described in the scope of patent claims. Examples thereof will be listed hereinafter.

In an X-ray CT device of an aspect of a first example, the above-mentioned image calculation unit or the above-mentioned background projection data calculation unit discriminates a region to be subjected to signal processing and a region other than that from the above-mentioned CT image or the above-mentioned background projection data. Deterioration of the CT value accuracy caused by the false image or the like can be prevented by performing smoothing by filtering on the above-mentioned signal processing region which has been discriminated, or by replacing the pixel value of the above-mentioned signal processing region with the X-ray absorption rate of the fixed value. In addition, there is an advantage that the CT value accuracy is not erroneously deteriorated by not processing a not-objected one which would be the cause.

In an X-ray CT device of an aspect of a second example, the above-mentioned image calculation unit or the above-mentioned background projection data calculation unit discriminates air and the region other than air from the above-mentioned CT image or the above-mentioned background projection data. Deterioration of the CT value accuracy caused by the false image or the like can be prevented by performing smoothing by filtering on the above-mentioned air region which has been discriminated, or by replacing the pixel value of the above-mentioned air region with the X-ray absorption rate of the fixed value.

In an X-ray CT device of an aspect of a third example, the above-mentioned image calculation unit or the above-mentioned background projection data calculation unit discriminates the region to be subjected to signal processing and the region other than that from the above-mentioned CT image or the above-mentioned background projection data. A false image is detected from the above-mentioned signal processing region which has been discriminated and the above-mentioned false image which has been detected is eliminated. Thus, deterioration of the CT value accuracy caused by the false image or the like can be prevented.

In an X-ray CT device of an aspect of a fourth example, the above-mentioned image calculation unit or the above-mentioned background projection data calculation unit detects the false image in accordance with a magnitude correlation between a predetermined threshold value and the above-mentioned CT image or the above-mentioned background projection data. Deterioration of the CT value accuracy caused by the false image or the like can be prevented by performing smoothing by filtering on the above-mentioned false image which has been detected, or by replacing the false image part with the X-ray absorption rate of the fixed value.

In an X-ray CT device of an aspect of a fifth example, the above-mentioned image calculation unit or the above-mentioned background projection data calculation unit discriminates the region to be subjected to signal processing and the region other than that from the above-mentioned CT image or the above-mentioned background projection data. Deterioration of the CT value accuracy caused by the false image or the like can be prevented by detecting a metal artifact from the above-mentioned signal processing region which has been discriminated and correcting the above-mentioned metal artifact which has been detected.

In an X-ray CT device of an aspect of a sixth example, the above-mentioned image calculation unit or the above-mentioned background projection data calculation unit discriminates the quantization error from the above-mentioned CT image or the above-mentioned background projection data. Deterioration of the CT value accuracy caused by the false image or the like can be prevented by correcting the above-mentioned CT image or the above-mentioned background projection data in accordance with the above-mentioned quantization error which has been discriminated.

In an X-ray CT device of an aspect of a seventh example, the above-mentioned image calculation unit or the above-mentioned background projection data calculation unit can prevent deterioration of the CT value accuracy caused by the false image or the like by applying smoothing to the above-mentioned CT image or the above-mentioned background projection data in accordance with the above-mentioned quantization error which has been discriminated.

In an X-ray CT device of an aspect of an eighth example, the above-mentioned image calculation unit or the above-mentioned background projection data calculation unit can prevent deterioration of the CT value accuracy caused by the false image or the like by switching the degree of the above mentioned smoothing in accordance with the X-ray absorption rate of the above-mentioned CT image or the integrated value of the above-mentioned background projection data.

In an X-ray CT device of an aspect of a ninth example, the above-mentioned image calculation unit or the above-mentioned background projection data calculation unit discriminates the quantization error from the above-mentioned CT image or the above-mentioned background projection data. It calculates the above-mentioned CT image by switching the resolution by changing the pixel size in accordance with the quantization error which has been discriminated. Thus, deterioration of the CT value accuracy caused by the false image or the like can be prevented.

DESCRIPTION OF REFERENCE NUMERALS

1 . . . X-ray tube, 2 . . . X-ray detector, 3 . . . gantry, 4 . . . rotating plate, 5 . . . table, 6 . . . subject, 7 . . . circular opening, 101 . . . input means, 102 . . . imaging means, 103 . . . image generation means, 111 . . . keyboard, 112 . . . mouse, 113 . . . memory, 114 . . . central processing unit, 115 . . . HDD device, 116 . . . gantry controller, 117 . . . X-ray control unit, 118 . . . table controller, 119 . . . DAS, 120 . . . memory, 121 . . . central processing unit, 122 . . . HDD device, 123 . . . monitor, 131 . . . imaging condition input unit, 132 . . . imaging control unit, 133 . . . imaging unit, 134 . . . signal acquisition unit, 135 . . . correction processing unit, 136 . . . reconstruction processing unit, 137 . . . image display unit, 141 . . . monitor screen, 142 . . . X-ray conditions, 143 . . . reconstruction range, 144 . . . processing object list, 151 . . . large FOV image calculation function, 152 . . . local measurement projection data calculation function, 153 . . . small FOV image calculation unit, 154 . . . analytical reconstruction function, 155 . . . processing object discrimination function, 156 . . . smoothing function, 157 . . . background image creation function, 158 . . . forward projection function, 159 . . . data comparison function, 160 . . . analytical reconstruction function, 161 . . . forward projection function, 162 . . . data comparison function, 163 . . . back projection processing function, 164 . . . image update function, 171 . . . to 184 . . . calculation steps of iterative reconstruction method, 191 . . . air region, 192 . . . region other than air, 193 . . . background projection data, 201 . . . background image creation function, 202 . . . forward projection function, 203 . . . processing object discrimination function, 204 . . . smoothing function, 205 . . . data comparison function, 211 . . . analytical reconstruction function, 212 . . . processing object discrimination function, 213 . . . forward projection function, 214 . . . smoothing function, 215 . . . data comparison function, 221 . . . processing object discrimination function, 222 . . . false image detection function, 223 . . . false image elimination function, 224 . . . background image creation function, 225 . . . forward projection function, 226 . . . data comparison function, 231 . . . false image, 232 . . . small FOV, 233 . . . enlarged region, 234 . . . profile, 235 . . . true value, 241 . . . processing object discrimination function, 242 . . . metal artifact detection function, 243 . . . metal artifact correction function, 244 . . . background image creation function, 245 . . . forward projection function, 246 . . . data comparison function, 251 . . . processing object discrimination function, 252 . . . smoothing function, 253 . . . background image creation function, 254 . . . forward projection function, 255 . . . data comparison function, 261 . . . enlarged region, 271 . . . processing object discrimination function, 272 . . . analytical reconstruction function, 273 . . . background image creation function, 274 . . . forward projection function, 275 . . . data comparison function.

The invention claimed is:

1. An X-ray CT device, including an X-ray generation unit for generating an X-ray, an X-ray detection unit for detecting the X-ray after transmitted through a subject, a projection data measurement unit for generating measurement projection data from a detection signal of the X-ray detection unit which has been measured by rotating the X-ray generation unit and the X-ray detection unit, and an image generation unit for generating a CT image from the measurement projection data, the image generation unit, comprising:
a background image creation unit for creating a CT image of a background region from the measurement projection data;
a background projection data calculation unit for calculating background projection data of the CT image of the background region on a path connecting the X-ray generation unit and the X-ray detection unit;
a local measurement projection data calculation unit for calculating local measurement projection data of a local region using the measurement projection data and the background projection data;
a local image calculation unit for calculating the CT image of the local region from the local measurement projection data;
a local projection data calculation unit for calculating local calculation projection data of the CT image of the local region on the path connecting the X-ray generation unit and the X-ray detection unit;
a local image correction unit for iteratively correcting the CT image of the local region on the basis of the local calculation projection data obtained by the local projection image calculation unit and the local measurement projection image;
and a cause elimination unit for eliminating a cause to deteriorate calculation accuracy of the background projection data from the background projection data.

2. The X-ray CT device according to claim 1, wherein the cause elimination unit includes a processing object discrimination unit for discriminating a processing object region to be subjected to signal processing and the other region from the background projection data.

3. The X-ray CT device according to claim 2, wherein the cause elimination unit performs smoothing by filtering on the processing object region that the processing object discrimination unit has discriminated, or replaces a pixel value of the processing object region with an X-ray absorption rate of a fixed value.

4. The X-ray CT device according to claim 2, wherein the processing object discrimination unit discriminates a region of air as the processing object region, and the cause elimination unit performs smoothing by the filtering on the region of air which has been discriminated, or replaces a pixel value of the region of air with an X-ray absorption rate of a fixed value.

5. The X-ray CT device according to claim 2, wherein the cause elimination unit detects a false image from the signal processing region that the processing object discrimination unit has discriminated and eliminates the false image which has been detected.

6. The X-ray CT device according to claim 5, wherein the cause elimination unit detects the false image in accordance with a magnitude correlation between a predetermined threshold value and the background projection data, and performs smoothing by filtering on the false image which has been detected, or replaces a pixel value of the false image with an X-ray absorption rate of a fixed value.

7. The X-ray CT device according to claim 1, wherein the background image creation unit is equipped with an image calculation unit for calculating a CT image from the measurement projection data, a projection data calculation unit for calculating calculation projection data as an integrated value of the CT image obtained from the measurement projection data on the path connecting the X-ray generation unit and the X-ray detection unit, and an image correction unit for iteratively correcting the CT image obtained from the measurement projection data such that the calculation projection data which has been obtained becomes equal to the measurement projection data, and divides the CT image which has been corrected into the local region and the background region to create the CT image of the background region.

8. The X-ray CT device according to claim 1, wherein the cause elimination unit discriminates a quantization error from the background projection data, and corrects the background projection data in accordance with the quantization error which has been discriminated.

9. The X-ray CT device according to claim 8, wherein the cause elimination unit applies smoothing on the background projection data in accordance with the quantization error which has been discriminated.

10. The X-ray CT device according to claim 9, wherein the cause elimination unit switches a degree of the smoothing in accordance with an integrated value of the background projection data.

11. The X-ray CT device according to claim 1, wherein the cause elimination unit discriminates a quantization error from the background projection data, and calculates the CT image by switching a resolution of the CT image of the background region in accordance with the quantization error which has been discriminated.

12. An image generation method for an image generation device equipped with a processing unit, for generating a CT image from measurement projection data of an X-ray CT device, the image generation method comprising:

creating, by the processing unit, a CT image of a background region from the measurement projection data;

calculating background projection data of the CT image of the background region on an X-ray irradiation path, and calculating local measurement projection data of a local region using the measurement projection data and the background projection data;

calculating a CT image of the local region from the obtained local measurement projection data;

calculating local calculation projection data of the CT image of the local region on the X-ray irradiation path;

iteratively correcting the CT image of the local region on the basis of the local calculation projection data which has been obtained and the local measurement projection data;

and eliminating a cause to deteriorate calculation accuracy of the background projection data from the background projection data.

13. The image generation method according to claim 12, comprising discriminating, by the processing unit, a processing object region to be subjected to signal processing and the other region from the background projection data, and performing smoothing by filtering on the processing object region which has been discriminated, or replacing a pixel value of the processing object region with an X-ray absorption rate of a fixed value.

14. The image generation method according to claim 12, comprising discriminating, by the processing unit, a processing object region to be subjected to signal processing and the other region from the background projection data, detecting a false image from the processing object region which has been discriminated, and eliminating the false image which has been detected.

15. The image generation method according to claim 12, comprising calculating the CT image from the measurement projection data when creating the CT image of the background region;

calculating calculation projection data as an integrated value of the CT image obtained from the measurement projection data on the X-ray irradiation path, and iteratively correcting the CT image obtained from the measurement projection data such that the calculation projection data which has been obtained becomes equal to the measurement projection data, and creating the CT image of the background region by dividing the CT image which has been corrected into the local region and the background region.

* * * * *